(12) United States Patent
Jackson

(10) Patent No.: US 10,415,041 B2
(45) Date of Patent: Sep. 17, 2019

(54) FUNCTIONAL LIGANDS TO TARGET MOLECULES

(71) Applicant: Base Pair Biotechnologies, Inc., Pearland, TX (US)

(72) Inventor: George W. Jackson, Pearland, TX (US)

(73) Assignee: Base Pair Biotechnologies, Inc., Pearland, TX (US)

( * ) Notice: Subject to any disclaimer, the term of this patent is extended or adjusted under 35 U.S.C. 154(b) by 0 days.

(21) Appl. No.: 15/893,532

(22) Filed: Feb. 9, 2018

(65) Prior Publication Data

US 2018/0237782 A1    Aug. 23, 2018

Related U.S. Application Data

(60) Provisional application No. 62/460,786, filed on Feb. 18, 2017, provisional application No. 62/456,847, filed on Feb. 9, 2017.

(51) Int. Cl.
| | |
|---|---|
| *C12N 15/11* | (2006.01) |
| *C12N 15/115* | (2010.01) |
| *C12N 15/10* | (2006.01) |

(52) U.S. Cl.
CPC ........ *C12N 15/115* (2013.01); *C12N 15/1048* (2013.01); *C12N 2310/16* (2013.01); *C12N 2330/31* (2013.01)

(58) Field of Classification Search
None
See application file for complete search history.

(56) References Cited

U.S. PATENT DOCUMENTS

2014/0178950 A1 *    6/2014    Franklin ................ C12N 15/52
                                                             435/134

* cited by examiner

*Primary Examiner* — Ekaterina Poliakova-Georgantas
(74) *Attorney, Agent, or Firm* — Equip Law Group; Christopher Quan

(57) ABSTRACT

The present invention relates functional ligands to target molecules, particularly to functional nucleic acids and modifications thereof, and to methods for simultaneously generating, for example, numerous different functional biomolecules, particularly to methods for generating numerous different functional nucleic acids against multiple target molecules simultaneously. The present invention further relates to functional ligands which bind with affinity to target molecules, such as amino acids, such as citrulline, and to target molecules such as crystallin or its subunits, such as alpha crystallin B-chain (CRYAB).

10 Claims, 5 Drawing Sheets

Specification includes a Sequence Listing.

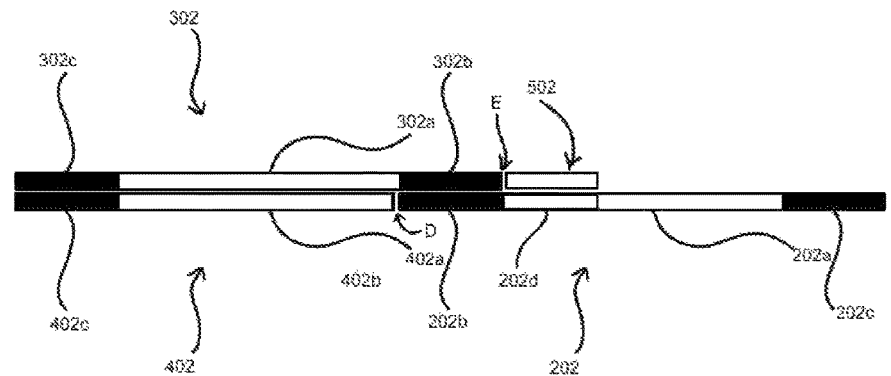
*Fig.6c.*
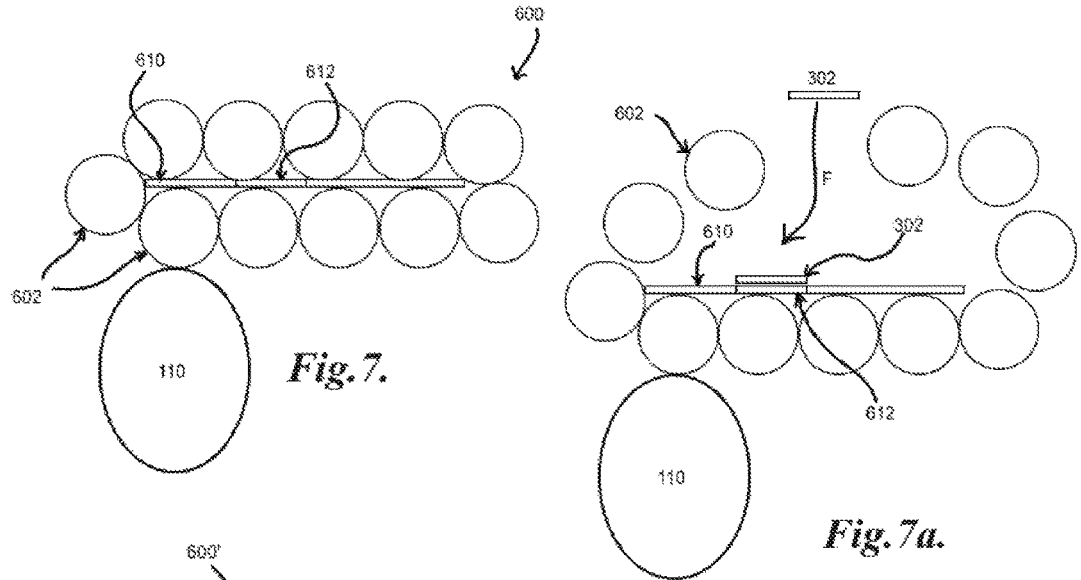
*Fig.7.* *Fig.7a.*
*Fig.7b.* *Fig.7c.*

FUNCTIONAL LIGANDS TO TARGET MOLECULES

CROSS-REFERENCE TO RELATED APPLICATIONS

This application claims the benefit and priority of the following U.S. provisional patent applications: Ser. No. 62/456,847, filed Feb. 9, 2017, entitled, "FUNCTIONAL LIGANDS TO CITRULLINE", and Ser. No. 62/460,786, filed Feb. 18, 2017, entitled, "FUNCTIONAL LIGANDS TO CRYSTALLIN", the contents all of which are hereby incorporated by reference in their entireties.

FIELD OF THE INVENTION

This invention relates to functional ligands to target molecules, particularly to functional nucleic acids and modifications thereof, more particularly to functional ligands with binding affinity to target molecules such as amino acids, such as citrulline, and to target molecules such as crystallin or its subunits, such as alpha crystallin B-chain (CRYAB).

SEQUENCE LISTING

Deoxyribonucleic acid (DNA) sequences, which are disclosed in the ASCII text file entitled "PCITRUS01_ST25.txt", created on Feb. 9, 2018 and of 85.5 KB in size, which is incorporated by reference in its entirety, herein are intended to include other aptamers incorporating modifications, truncations, incorporations into larger molecules or complexes, and/or other aptamers having substantial structural or sequence homology, for example, greater than 75% sequence homology, as well as RNA and/or other non-DNA/RNA aptamers. The disclosed aptamers may also bind to homologous proteins or molecules from organisms other than the organisms listed herein, to recombinant or non-recombinant versions of the proteins or molecules, to modified versions of the proteins or molecules, to proteins or molecules from sources other than the source listed herein. The aptamers are artificial, non-naturally occurring sequences designed and/or selected for specific and/or high affinity binding to a target molecule. Non-naturally occurring sequences of aptamers, may also not be present in naturally occurring systems or situations, such as by, for example, not being already present or having a pre-existing function in a naturally occurring setting. The indication of the species and source of the target proteins or molecules is given for reference only and is not intended to be limiting. Without limitation as to target molecules to which they may bind and without being bound to any particular theory, SEQ IDs 1-230 may generally bind to the target molecule citrulline, and SEQ IDs 233-332 may generally bind to the target molecule alpha crystallin B-chain (CRYAB). SEQ ID 231 may generally be utilized as a leading or priming sequence appended to the 5'-end of any of the aptamer sequences binding to citrulline, SEQ IDs 1-230, and SEQ ID 232 may generally be utilized as a trailing or priming sequence appended to the 3'-end of any of the aptamer sequences binding to citrulline, SEQ IDs 1-230, or vice versa or any combination thereof.

BACKGROUND OF THE INVENTION

Aptamers, which are nucleic acid ligands capable of binding to molecular targets, have recently attracted increased attention for their potential application in many areas of biology and biotechnology. They may be used as sensors, therapeutic tools, to regulate cellular processes, as well as to guide drugs to their specific cellular target(s). Contrary to the actual genetic material, their specificity and characteristics are not directly determined by their primary sequence, but instead by their secondary and/or tertiary structure. Aptamers have been recently investigated as immobilized capture elements in a microarray format. Others have recently selected aptamers against whole cells and complex biological mixtures. Aptamers are typically characterized by binding to their target molecules via non-Watson-Crick (i.e. non-hybridization) mechanisms, such as by intermolecular forces resulting from the secondary or tertiary structure of the aptamer. This is especially true of non-nucleic acid target molecules where Watson-Crick mechanisms typically do not apply.

Aptamers are commonly identified by an in vitro method of selection sometimes referred to as Systematic Evolution of Ligands by EXponential enrichment or "SELEX". SELEX typically begins with a very large pool of randomized polynucleotides which is generally narrowed to one aptamer ligand per molecular target. Once multiple rounds (typically 10-15) of SELEX are completed, the nucleic acid sequences are identified by conventional cloning and sequencing. Aptamers have most famously been developed as ligands to important proteins, rivaling antibodies in both affinity and specificity, and the first aptamer-based therapeutics are now emerging. More recently, however, aptamers have been also developed to bind small organic molecules and cellular toxins, viruses, and even targets as small as heavy metal ions.

Citrulline is an a-amino acid. It is a key intermediate in the urea cycle, the pathway by which mammals excrete ammonia. In the human body, citrulline is produced as a byproduct of the enzymatic production of nitric oxide from the amino acid arginine, catalyzed by nitric oxide synthase. Several proteins contain citrulline as a result of a posttranslational modification. These citrulline residues are generated by a family of enzymes called peptidylarginine deiminases (PADs), which convert arginine into citrulline in a process called citrullination or deimination. Proteins that normally contain citrulline residues include myelin basic protein (MBP), filaggrin, and several histone proteins, whereas other proteins, such as fibrin and vimentin are susceptible to citrullination during cell death and tissue inflammation. Circulating citrulline concentration is a biomarker of intestinal functionality.

Crystallin is a water-soluble structural protein found in the lens and the cornea of the eye accounting for the transparency of the structure. Alpha-crystallin occurs as large aggregates, comprising two types of related subunits (A and B) that are highly similar to the small (15-30 kDa) heat shock proteins (HSPs), particularly in their C-terminal halves. The relationship between these families is one of classic gene duplication and divergence, from the small HSP family, allowing adaptation to novel functions. Divergence probably occurred prior to evolution of the eye lens, alpha-crystallin being found in small amounts in tissues outside the lens. Alpha-crystallin has chaperone-like properties including the ability to prevent the precipitation of denatured proteins and to increase cellular tolerance to stress. It has been suggested that these functions are important for the maintenance of lens transparency and the prevention of cataracts. This is supported by the observation that alpha-crystallin mutations show an association with cataract formation. Alpha crystallin B-chain (CRYAB) is one of the subunits that forms alpha-crystallin.

SUMMARY OF THE INVENTION

The present invention relates functional ligands to target molecules, particularly to functional nucleic acids and modifications thereof, and to methods for simultaneously generating, for example, numerous different functional biomolecules, particularly to methods for generating numerous different functional nucleic acids against multiple target molecules simultaneously. The present invention further relates to functional ligands which bind with affinity to target molecules, more particularly to functional ligands with binding affinity to target molecules such as amino acids, such as citrulline, and to target molecules such as crystallin or its subunits, such as alpha crystallin B-chain (CRYAB). The present invention further relates to methods for generating, for example, functional biomolecules, particularly to functional nucleic acids, that bind with functional activity to another biomolecule, such as a receptor molecule. More than one or multiple targets as used herein may generally include different types of targets, and/or may also include a multitude of a singular type of targets at different conditions, such as, for example, temperature, pH, chemical environment, and/or any other appropriate conditions.

In general, a method for generating functional biomolecules includes obtaining a library, such as a diverse or randomized library, for example, of biomolecules. Biomolecules may generally include nucleic acids, particularly single-stranded nucleic acids, peptides, other biopolymers and/or combinations or modifications thereof. A library of biomolecules may include nucleic acid sequences, such as ribonucleic acid (RNA), deoxyribonucleic acid (DNA), artificially modified nucleic acids, and/or combinations thereof. The method for generating functional biomolecules further includes contacting the library of biomolecules with more than one target, such as, for example, a molecular target, material and/or substance. In general, the members of the library that do not bind with some affinity to the more than one target may be washed or otherwise partitioned from the remainder of the library, which may have a given level of binding affinity to the more than one target. The process may be repeated to partition the strongest binding members of the library. Amplification of the biomolecules may also be utilized to increase the numbers of the binding members of the library for subsequent repetitions and for isolation and/or purification of any final products of the process. Embodiments of the SELEX method may generally be utilized to achieve the generation of functional biomolecules of a given binding affinity, such biomolecules generally referred to as aptamers or ligands.

In one exemplary aspect of the invention, generation of functional biomolecules may be performed against more than one or multiple targets simultaneously within a single system, such as the generation of functional nucleic acid ligands within a single reaction volume. In general, more than one or a plurality of targets may be disposed within in a single reaction volume, and a library of biomolecules, such as a nucleic acid library, may be applied to the reaction volume. The members of the library that do not bind to any of the plurality of targets under given conditions may then be partitioned, such as by washing. One or more rounds of binding and partitioning of the members of the library may be performed, such as, for example, to obtain a remainder of members of the library with a given affinity for their targets. The remaining members that bind to the plurality of targets of the library may then be marked and/or tagged, such as to identify the particular target or targets to which the member(s) of the library binds. The binding members of the library may then be isolated and, by virtue of the marking or tagging, be matched to a particular target or targets. This is desirable as high capacity, multiplexed identification procedures may save time, expense, and physical space for the process over single target identification processes. The present method may also be desirable as it may be utilized to identify and/or eliminate biomolecules that bind or have a tendency to bind to multiple targets.

In an exemplary embodiment, a plurality of target molecules are affixed to a substrate within a single reaction volume, such as, for example, by attaching the targets to a substrate of an array. It may generally be appreciated that a single reaction volume may refer to or include multiple reaction sub-volumes, such as, for example, discrete or semi-discrete fluid droplets. In general, the targets may be disposed with multiple copies of each target in clusters or "spots" such that a given array may have an ordered deposition of targets on the substrate, with each target identifiable by the location of a particular spot on the substrate. A library of nucleic acids may then be contacted or applied to the array and the non-binding members of the library may be partitioned or washed off the array. The binding and washing steps may be repeated and may also utilize an amplification step to generate additional copies of any remaining binding members of the library. The array may then be marked or tagged with a plurality of identifiers, such as, for example, a plurality of oligonucleotides which may universally bind through Watson-Crick interactions to the members of the library of nucleic acids. The marking or tagging may be, for example, accomplished by manually applying identifiers, such as by pipetting or the like, utilizing microcontact pins, applying membranes/films with identifiers, printing, for example, inkjet printing, and/or other similar tagging methods, of identifier containing solutions to the array. The identifiers may further include a unique or semi-unique sequence which may be utilized to correspond to the spots and thus the targets of the array. For example, a unique or semi-unique identifier sequence may be utilized that identifies each spatial location on an array, such as each particular target spot. The identifier may then be associated with and/or attached to the nucleic acid members bound to a particular spot. Thus, the nucleic acids, for example, bound to a particular target spot may be identified by the sequence of the associated identifier. In some embodiments, the identifiers may further be primers and may be utilized with a nucleic acid amplification reaction on the array to generate additional copies of the bound nucleic acids. The unique or semi-unique identifier sequence may also be incorporated into the members of the library amplified. This may be desirable for associating a given member with a target or targets while preserving the particular sequence of the member as the locational identifying sequence is appended to the sequence of the library member. This may be particularly desirable for resolving multiple binders to a single target or members of the library that bind to multiple targets.

In general, the starting library of biomolecules, such as nucleic acids, may be the product of at least one round of a previous SELEX protocol. For example, at least one round of SELEX may be performed with a library of biomolecules against multiple targets, such as, for example, in a solution. The targets in the solution may be substantially identical to the targets disposed on an array. This may be desirable as multiple rounds of selection may be performed with a library prior to applying the remaining members to an array for marking/tagging. Complex target arrays may generally be more expensive and/or difficult to make or utilize than solutions of target molecules, so performing only the final binding and marking/tagging procedure on the array may be desirable.

In other embodiments, identifiers may be predisposed on the array substrate in substantial proximity to the spots such that they may bind to, for example, nucleic acids bound to the target spots. The identifiers may, for example, be covalently attached to the substrate. In some embodiments, the attachments may be controllably breakable or cleavable such that the identifiers may be released from the substrate such that they may, for example, more easily bind to the bound nucleic acids on the spots.

In further embodiments, identifiers may be synthesized in situ on the array, such as by light directed in situ nucleic acid synthesis. Appropriately sequenced identifiers may then be synthesized in proximity to particular spots such that the newly synthesized identifiers may bind to the nucleic acids bound to the target spot.

In still other embodiments, identifiers may be disposed and/or synthesized on a separate substrate, such as a membrane, in a spatial disposition that substantially matches the spatial disposition of spots on the array, i.e. the identifiers may be arranged such that they may be readily superimposed onto the target spots on the array. The identifier substrate may then be contacted with the array with locational matching of the spots with identifiers. The identifiers may then bind to the nucleic acids bound to the target spots. Any appropriate method of facilitating binding may be utilized, such as, for example, actions to drive migration of the identifiers to the array, such as capillary action, electrophoresis, pressure, gravitational settling, and/or any other appropriate method or combination thereof. The separate substrate may also be soluble, erodible, substantially permeable to the identifiers, and/or otherwise adapted for facilitating migration of the identifiers to the array.

In yet still other embodiments, the array substrate may be physically divided and/or partitioned for separate collection of the, for example, nucleic acids bound to the spots. The spots may, for example, also be controllably removable from the substrate such that they may be individually recovered and sorted.

In still yet other embodiments, identifiers may be disposed and/or synthesized on a separate substrate, such as a membrane, in a spatial disposition that substantially matches the spatial disposition of spots on the array, i.e. the identifiers may be arranged such that may be readily superimposed onto the target spots on the array. The separate substrate may be kept separately while the array substrate maybe physically divided and/or partitioned for separate collection of the nucleic acids bound to the spots. In this manner, the location of the different nucleic acids maybe maintained even when the array substrate is no longer intact, if the locations are of value. The identifiers may also be selectively applied to particular locations on the array and/or applied in a particular order or in groups.

In some embodiments, identifiers may only be applied to spots with bound nucleic acids. The spots with bound nucleic acids may be detected, for example, by detecting the presence of nucleic acids, such as by applying nucleic acid binding dyes, such as SYBR dyes, ethidium bromide and/or other appropriate dyes. The members of the nucleic acid library may also include detectable portions, such as, for example, fluorescent moieties, radioactive tags and/or other appropriate detectable portions.

In some embodiments, the identifiers may be applied to the bound nucleic acids together with other materials, such as for example, components of a nucleic acid amplification reaction, a nucleic acid ligation reaction, photo-linking reagents, and/or any other appropriate material, such as those materials that may facilitate attachment or association of the identifiers to the bound nucleic acids.

In yet another embodiment, identifiers may be ligated to the, for example, bound nucleic acids. For example, a nucleic acid ligase may be utilized to covalently link an identifier sequence to the bound nucleic acid. Further nucleic acid fragments may be utilized to facilitate ligase action, such as appropriate complementary fragments that may aid the formation of a substantially double-stranded nucleic acid complex compatible with a ligase. For another example, photo-ligation may be used to attach the identifiers to the, for example, bound nucleic acids. Photo-ligation may be especially useful when certain substrates are used. For example, macro-porous substrates.

In general, methods may be applied that may facilitate binding or other interactions between the identifiers and the, for example, nucleic acids bound to the spots. For example, the temperature may be increased to dissociate the nucleic acids from the spots. The temperature may subsequently be lowered such that, for example, base pairing may occur between the nucleic acids and the identifiers. Further in general, it may be desirable to apply the identifiers in a manner that physically separates and/or isolates the individual target spots such that cross-marking due to identifier diffusion/migration may be minimized. For example, the identifiers may be applied in individual fluid droplets such that there is no continuous fluid contact between individual identifier containing fluids. For further example, the substrate of the array may be absorbent and/or porous such that the identifiers may be absorbed into the substrate material. The substrate material may also block lateral diffusion while allowing vertical diffusion, such that identifiers may be applied and absorbed into the substrate while minimizing diffusion across the plane of the substrate, such as to other target spots.

In a further embodiment, a method for generating functional biomolecules includes obtaining a library of peptide sequences and contacting the library with a plurality of targets. In some exemplary embodiments, the peptide sequence may be tagged, linked, marked and/or otherwise associated with a nucleic acid sequence. The nucleic acid sequence may be, for example, representative of the sequence of the peptide. For example, the nucleic acid may substantially encode the peptide sequence. Also for example, the nucleic acid may be a unique or semi-unique identifier sequence. The nucleic acid sequence may then be utilized to bind another identifier, as described above, such that a peptide bound to a target may be tagged or marked as to which target it bound.

In an exemplary embodiment, a bacteriophage (phage) may be generated that includes a peptide sequence of interest in its protein coat. The phage may further include a nucleic acid sequence that may be representative of the peptide sequence within the nucleic acid of the phage. The phage may then be contacted with a plurality of targets, as above. This may generally be referred to as phage display. Non-binding phages may be washed and/or partitioned, while binding phages may be tagged or marked with identifiers, as above. As phage nucleic acids are generally contained within the protein coat of the phage, the nucleic acid may generally be exposed for binding to the identifier. For example, the phage may be heated such that the protein coat denatures and/or disassembles such that the nucleic acid is exposed. The identifier may also be introduced into the phage, such as by electroporation, electrophoresis, and/or any other appropriate method.

Other methods of peptide selection may include, but are not limited to, mRNA display, ribosome display, and/or any other appropriate peptide display method or combination thereof.

In another aspect of the invention, methods for handling and sorting the resultant sequences of a multiplexed binding process are provided. In some embodiments, the sequences may be sorted by identifier sequences to establish which target or targets the sequence bound. The sequences may further be compared, aligned and/or otherwise processed to identify features, characteristics and/or other useful properties, relationships to each other, and/or target properties.

In a further aspect of the invention, methods for monitoring and/or controlling the diversity of the library of biomolecules may be utilized. For example, too few rounds of selection may result in a biomolecule pool with too many weak binding members while too many rounds of selection may result in only a few binding members, such as members corresponding to only a few targets rather than members corresponding to all of the targets present. In one embodiment, Cot analysis may be employed to measure and/or monitor the diversity of the library of biomolecules through multiple rounds of selection. Cot, or Concentration×time, analysis measures the annealing time of particular oligonucleotides while in solution with other nucleic acids, such as the members of the library of biomolecules. In general, the annealing time will be faster the lower the diversity of the library.

The present invention together with the above and other advantages may best be understood from the following detailed description of the embodiments of the invention illustrated in the drawings.

BRIEF DESCRIPTION OF THE FIGURES

FIGS. 6, 6a, 6b and 6c illustrate embodiments of identifiers and ligation of identifiers to a library member;

FIGS. 7 and 7a illustrate phage display for a target;

FIG. 7b illustrates an mRNA display fusion product;

FIG. 7c illustrates a ribosome display fusion product;

DETAILED DESCRIPTION OF THE INVENTION

Figure 1:
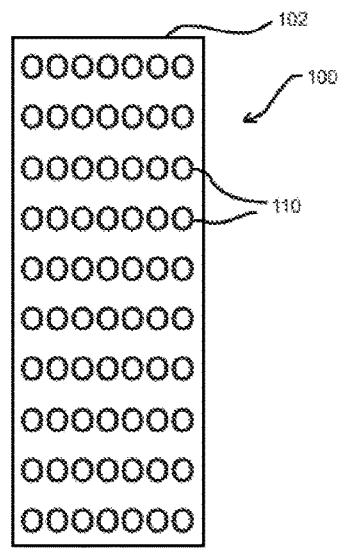
FIG. 1 illustrates an embodiment of a multiple target array.

The detailed description set forth below is intended as a description of the presently exemplified methods, devices, and compositions provided in accordance with aspects of the present invention and is not intended to represent the only forms in which the present invention may be practiced or utilized. It is to be understood, however, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the exemplified methods, devices and materials are now described.

The present invention relates functional ligands to target molecules, particularly to functional nucleic acids and modifications thereof, and to methods for simultaneously generating, for example, numerous different functional biomolecules, particularly to methods for generating numerous different functional nucleic acids against multiple target molecules simultaneously. The present invention further relates to functional ligands which bind with affinity to target molecules, more particularly to functional ligands with binding affinity to target molecules such as amino acids, such as citrulline, and to target molecules such as crystallin or its subunits, such as alpha crystallin B-chain (CRYAB), which may also include their derivatives, isomers and/or breakdown products. The present invention further relates to methods for simultaneously generating different functional biomolecules, particularly to functional nucleic acids, that bind with functional activity to another biomolecule, such as a receptor molecule. Functional ligands, particularly functional nucleic acids, of the present invention are generally artificial, non-naturally occurring sequences designed and/or selected for specific and/or high affinity binding to target molecules such as amino acids, such as citrulline, and to target molecules such as crystallin or its subunits, such as alpha crystallin B-chain (CRYAB). Non-naturally occurring sequences of functional nucleic acids, such as aptamers, may also be useful by interacting with a target molecule in a manner not present in naturally occurring systems or situations, such as by, for example, not being already present or having a pre-existing function in a naturally occurring setting.

In general, a method for generating functional biomolecules includes obtaining a library, such as a diverse or randomized library, of biomolecules. Biomolecules may generally include nucleic acids, particularly single-stranded nucleic acids, peptides, other biopolymers and/or combinations or modifications thereof. A library of biomolecules may include nucleic acid sequences, such as ribonucleic acid (RNA), deoxyribonucleic acid (DNA), artificially modified nucleic acids, and/or combinations thereof. In general, modified nucleic acid bases may be utilized and may include, but are not limited to, 2'-Deoxy-P-nucleoside-5'-Triphosphate, 2'-Deoxyinosine-5'-Triphosphate, 2'-Deoxypseudouridine-5'-Triphosphate, 2'-Deoxyuridine-5'-Triphosphate, 2'-Deoxyzebularine-5'-Triphosphate, 2-Amino-2'-deoxyadenosine-5'-Triphosphate, 2-Amino-6-chloropurine-2'-deoxyriboside-5'-Triphosphate, 2-Aminopurine-2'-deoxyribose-5'-Triphosphate, 2-Thio-2'-deoxycytidine-5'-Triphosphate, 2-Thiothymidine-5'-Triphosphate, 2'-Deoxy-L-adenosine-5'-Triphosphate, 2'-Deoxy-L-cytidine-5'-Triphosphate, 2'-Deoxy-L-guanosine-5'-Triphosphate, 2'-Deoxy-L-thymidine-5'-Triphosphate, 4-Thiothymidine-5'-Triphosphate, 5-Aminoallyl-2'-deoxycytidine-5'-Triphosphate, 5-Aminoallyl-2'-deoxyuridine-5'-Triphosphate, 5-Bromo-2'-deoxycytidine-5'-Triphosphate, 5-Bromo-2'-deoxyuridine-5'-Triphosphate, 5-Fluoro-2'-deoxyuridine-5'-Triphosphate, 5-Trifluoromethyl-2-deoxyuridine-5'-Triphosphate, and/or any other appropriate modified nucleic acid base. It may generally be understood that the nucleoside triphosphates (NTPs) listed above may generally refer to any appropriate phosphate of the modified base, such as additionally, for example, monophosphates (NMPs) or diphosphates (NDPs) of the base. The method for generating functional biomolecules further includes contacting the library of biomolecules with at least one target, such as, for example, a molecular target, material and/or substance. In general, the members of the library that do not bind with some affinity to the target may be washed or otherwise partitioned from the remainder of the library, which may have a given level of binding affinity to the target. The process may be repeated to partition the strongest binding members of the library. Amplification of the biomolecules may also be utilized to increase the numbers of the binding members of the library for subsequent repetitions and for isolation and/or purification of any final products of the process. Embodiments of the SELEX method may generally be utilized to achieve the generation of functional biomolecules of a given binding affinity. The basic SELEX protocol and aptamers are described in U.S. Pat. No. 5,270,163, entitled "Methods for identifying nucleic acid ligands," the entire contents of which are hereby incorporated by reference.

In one exemplary aspect of the invention, generation of functional biomolecules may be performed against multiple targets simultaneously within a single system, such as the generation of functional nucleic acid ligands within a single reaction volume. In general, a plurality of targets may be disposed within in a single reaction volume and a library of biomolecules, such as a nucleic acid library, may be applied to the reaction volume. The targets may be, for example, proteins, cells, small molecules, biomolecules, and/or combinations or portions thereof. The members of the library that do not bind to any of the plurality of targets under given conditions may then be partitioned, such as by washing. The remaining members of the library may then be marked and/or tagged, such as to identify the particular target or targets to which the member of the library binds. The binding members of the library may then be isolated and, by virtue of the marking or tagging, be matched to a particular target or targets. This may be desirable as high capacity, multiplexed identification procedures may save time, expense, and physical space for the process over single target identification processes. The present method may also be desirable as it may be utilized to identify and/or eliminate molecules that bind to multiple targets.

Functional ligands to amino acids such as citrulline, without limitation and without being bound to any particular theory, may be utilized for detection, quantification, and/or other diagnostic applications, such as for detection of citrulline, in body fluids or tissues or for purification, separation or other forms of analysis or processing. For example, detection of citrulline may be utilized in bodily fluids as a biomarker for intestinal function in humans or for detecting citrullinated proteins, such as those involved in rheumatoid arthritis.

Functional ligands to CRYAB, without limitation and without being bound to any particular theory, may be utilized for detection, quantification, and/or other diagnostic applications, such as for detection of CRYAB in tissues or body fluids for characterization of disease, or for therapeutic uses, such as for binding to CRYAB to prevent aberrant aggregate formations of CRYAB in the eye, for example, which may form cataracts or other visual impairment due to light scattering.

Figure 2:
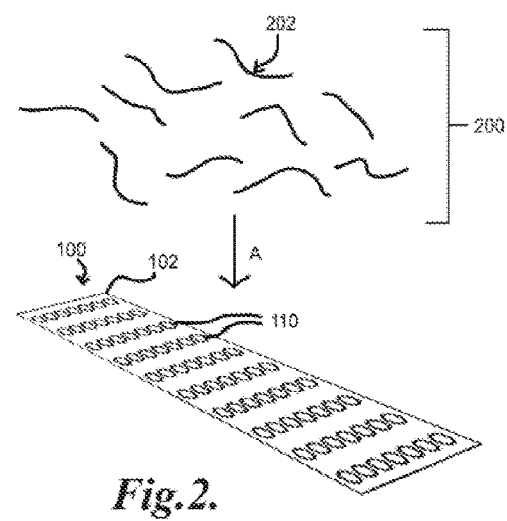
FIG. 2 illustrates the application of a library of biomolecules to a target array.
Figure 2A:
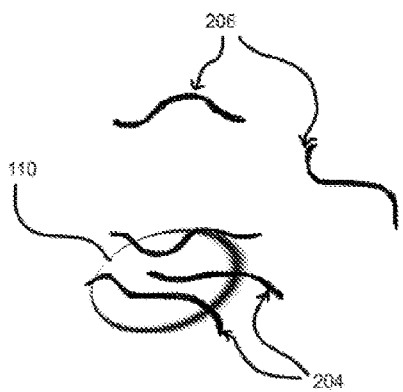
FIG. 2a illustrates the binding of members of a library of biomolecules to a target spot.
Figure 3:
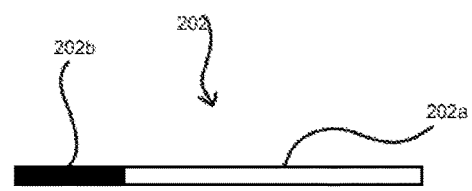
FIGS. 3 and 3a illustrate embodiments of biomolecule library members.
Figure 3A:
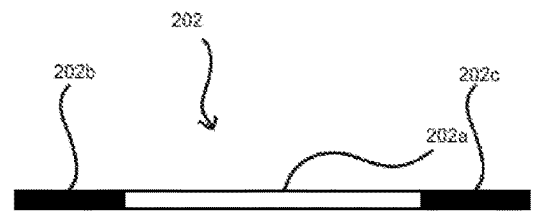
Figure 3B:
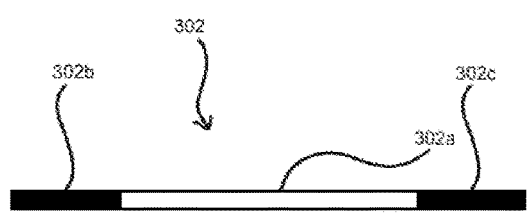
FIG. 3b illustrates an embodiment of an identifier.
Figure 4:
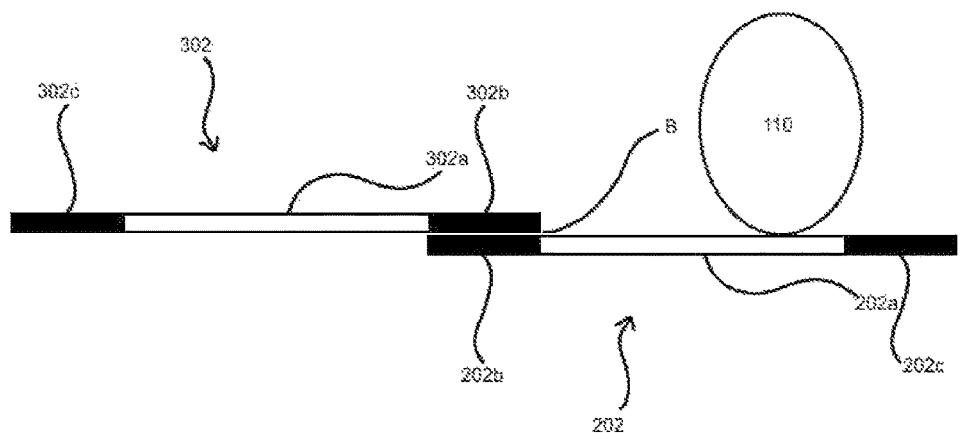
FIG. 4 illustrates the tagging of a library member bound to target with an identifier.
Figure 4A:
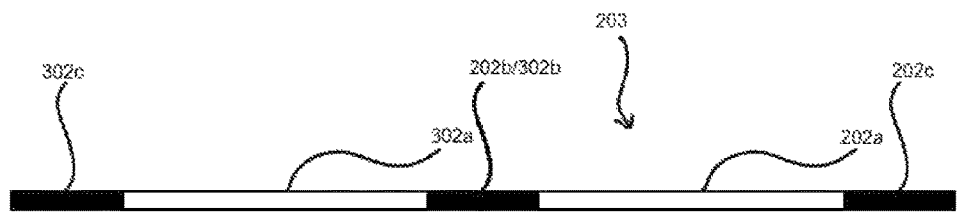
FIG. 4a illustrates a tagged library member product.

In an exemplary embodiment, a plurality of target molecules are affixed to a substrate within a single reaction volume, such as, for example, by attaching the targets to a substrate of an array. As illustrated in FIG. 1, the targets may be disposed with multiple copies of each target, such as target molecules, in clusters or "spots" 110 on the substrate 102 of an array 100 such that a given array 100 may have an ordered deposition of targets on the substrate 102, with each target identifiable by the location of a particular spot 110 on the substrate 102. Each spot 110 may be a unique target or there may be multiple spots 110 of at least one target on a given array 100. In general, high content target arrays, such as high content protein or antibody arrays or other forms of arrays recognized as high content or high density for interrogating a high number of different targets at once may be utilized. For example, human protein microarrays, such as ProtoArray® from ThermoFisher containing over 9,000 unique proteins in spotted format, may be utilized. A library 200 of, for example, nucleic acids 202 may then be applied A to array 100, as illustrated in FIG. 2. Particular members 204 of the library 200 may then bind to target spots 110, such as illustrated in FIG. 2a. The non-binding members 206 of the library 200 may be partitioned or washed off the array 100. The binding and washing steps may be repeated and may also utilize an amplification step to generate additional copies of any remaining binding members 204 of the library 200. The array 100 may then be marked or tagged with a plurality of identifiers, such as, for example, a plurality of oligonucleotides which may universally bind through Watson-Crick interactions to the members of the library of, for example, nucleic acids. In one embodiment, each member 202 of the library 200 may include a potential binding sequence 202a and at least one conserved region 202b which may bind an identifier oligonucleotide, such as illustrated in FIG. 3. A further conserved region 202c may also be included to facilitate priming for amplification or extension reactions, such as Polymerase Chain Reaction (PCR), as illustrated in FIG. 3a. In general the conserved regions 202b, 202c may flank the potential binding sequence 202a, such as to facilitate priming for amplification. An identifier 302 may then include a unique or semi-unique sequence 302a, such as illustrated in FIG. 3b, which may be utilized to correspond to the spots 110 and thus the targets of the array 100 by location of the a spot 110 on the substrate 102. The identifiers 302 may further include conserved region 302b which may bind to the conserved region 202b of the library members 202 by Watson-Crick base pairing. The identifiers 302 may also include a further conserved region 302c which may facilitate priming for amplification. The identifiers 302 may be, for example, applied to the spots 110 by printing, for example, inkjet printing, using micro-contact pins, and/or otherwise applying solutions containing identifiers 302 to the substrate 102 of the array 100, such as, for example, by pipetting or the like, onto the spots 110. A library member 202 bound to a target spot 110 may then be tagged with an identifier 302 via base pairing B at regions 202b, 302b, as illustrated in FIG. 4. Thus, the nucleic acids 202 bound to a particular target spot 110 may be identified by the sequence 302a of the identifier 302. In an exemplary embodiment, nucleic acid amplification or extension, such as PCR, may be utilized to generate copies of the members 202 bound to the spots 110, incorporating the identifier sequence 302a (or more its complementary sequence) into the product 203, as illustrated in FIG. 4a. This may be desirable for associating a given member 202 with a target or targets 110 while preserving the particular sequence of the member 202. This may be particularly desirable for resolving multiple binders to a single target or members of the library that bind to multiple targets. Subsequent amplifications may utilize primers for the sequences 202c, 302c such that only the products 203 containing both the sequences 202a, 302a are amplified. It may be understood that references to nucleic acid sequences, such as above, may generally refer to either a particular sequence or the corresponding complementary nucleic acid sequence. In general, it may be desirable for single droplets and/or otherwise separated volumes of solutions containing identifiers 302 for each spot 110 on the array 100 such that the possibility of mistagging may be reduced.

In one aspect, the identifiers may be printed on all the targets. In another aspect, the identifiers may be printed only on targets with bound biomolecules.

Figure 8:
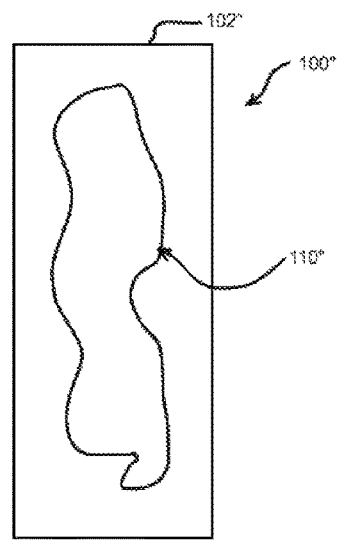
FIG. 8 illustrates an example of a histology section target.

In another embodiment, a histology section, such as the section 110" on substrate 102" of histology slide 100" in FIG. 8, may be utilized as a target set. The section 110" may be, for example, a tissue section, a cell mass, and/or any other appropriate biological sample which may generally have structurally significant features. As with the array 100, a library of biomolecules, such as nucleic acids, may be applied which may bind to specific locations on the section 110", the locations on which may, for example, represent separate targets to generate affinity binding nucleic acids. Identifiers may then be disposed on the slide 100" as described above, or as in the embodiments below, such that identifiers may be utilized to correspond to specific features of the section 110".

Figure 5:
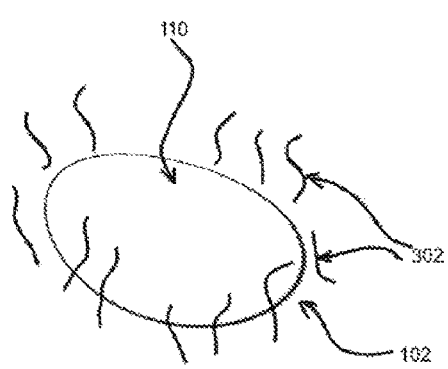
FIG. 5 illustrates a target spot with nearby identifiers on a substrate.

In other embodiments, identifiers may be predisposed on the array substrate in substantial proximity to the spots, such as illustrated with identifiers 302 disposed on substrate 102 in proximity to spot 110 in FIG. 5, such that they may bind to nucleic acids bound to the target spots. The identifiers may, for example, be covalently attached to the substrate. In some embodiments, the attachments may be controllably breakable or cleavable such that the identifiers may be released from the substrate such that they may, for example, more easily bind to the bound nucleic acids on the spots.

In further embodiments, identifiers may be synthesized in situ on the array, such as by light directed in situ nucleic acid synthesis. Appropriately sequenced identifiers may then be synthesized in proximity to particular spots such that the newly synthesized identifiers may bind to the nucleic acids bound to the spot.

Figure 5A:
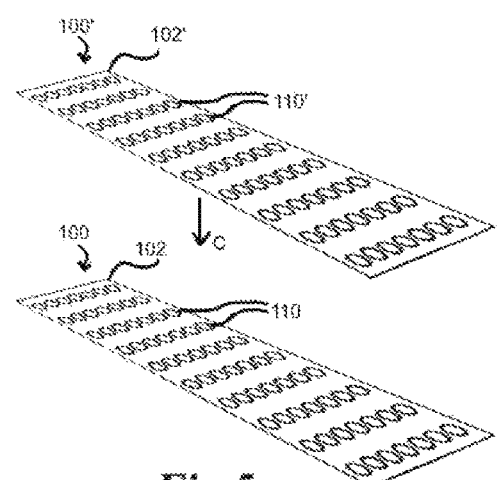
FIG. 5a illustrates the application of an identifier sheet to a target array.

In still other embodiments, identifiers may be disposed and/or synthesized on a separate substrate, such as a membrane, in a spatial disposition that matches the spatial disposition of spots on the array. FIG. 5a illustrates an example of an identifier sheet 100' with membrane 102' which may include identifier spots 110' which may substantially correspond to target spots 110 of the array 100. The identifier sheet 100' may then be contacted C with the array 100 with locational matching of the target spots 110 with identifier spots 110'. The identifiers may then bind to the nucleic acids bound to the target spots. Any appropriate method of facilitating binding may be utilized, such as, for example, actions to drive migration of the identifiers to the array, such as capillary action, electrophoresis, pressure, gravitational settling, and/or any other appropriate method or combination thereof.

In some embodiments, the membrane may be soluble and/or substantially erodible. For example, the membrane may include a film forming and/or soluble material. Identifiers and/or other materials, such as components of a nucleic acid amplification or ligation reaction, may be included such that a film is formed containing the desired materials. The membrane may then be applied to the substrate and a suitable solvent, such as water or ethanol, may be utilized to dissolve and/or erode the film, which may then release the included materials, such as the identifiers, to the substrate. Suitable materials for the film may include hydrophilic materials including polysaccharides such as carrageenan, chondroitin sulfate, glucosamine, pullulan, soluble cellulose derivatives such as hydroxypropyl cellulose and hydroxymethyl cellulose, polyacrylic acid, polyvinyl alcohol, polyethylene glycol (PEG), polyethylene oxide (PEO), ethylene oxide-propylene oxide co-polymer, polyvinylpyrrolidone (PVP), polycaprolactone, polyorthoesters, polyphosphazene, polyvinyl acetate, and polyisobutylene.

The membrane may further be adapted to have a desirable rate of erosion and/or dissolution. The rate may be modified by the inclusion of hydrophobic and/or less soluble additives. Suitable materials may include, but are not limited to, those from the family of quaternary ammonium acrylate/methacrylate co-polymers, (Eudragit RS), cellulose and its lower solubility derivatives, such as butyl cellulose, hydroxybutyl cellulose and ethylhydroxyethyl cellulose, high molecular weight PEG or PEO or a combination thereof.

In yet still other embodiments, the array substrate may be physically divided and/or partitioned for separate collection of the nucleic acids bound to the spots. The spots may, for example, also be controllably removable from the substrate such that they may be individually recovered and sorted. The array itself may also be perforated and/or otherwise easily and/or conveniently partitionable.

In another embodiment, identifiers may be ligated to the bound nucleic acids. For example, a nucleic acid ligase may be utilized to covalently link an identifier sequence to the bound nucleic acid. In general, nucleic acid ligases are enzymes that covalently join two nucleic acids by catalyzing the formation of phosphodiester bonds at the ends of the phosphate backbone of the nucleic acids. Examples of appropriate nucleic acid ligases may include, but are not limited to, E. coli DNA ligase, T4 DNA ligase, T4 RNA ligase, strand break DNA repair enzymes, and/or any other appropriate ligase, modified enzyme, and/or a combination thereof. In general the ligase utilized may be selected based on the form of ligation performed, such as ligation of blunt ends, compatible overhang ("sticky") ends, single stranded DNA, singe stranded RNA and/or any other form of ligation. Further in general, the steps in ligating two nucleic acids together is a one step process that may be carried out at or near room temperature. Further nucleic acid fragments may be utilized to facilitate ligase action, such as appropriate complementary fragments that may aid the formation of a substantially double-stranded nucleic acid complex compatible with a ligase. In general, double stranded ligation may be employed and may utilize substantially compatible overhang fragments to facilitate ligation, or also blunt end ligation may be utilized, such as with either the nucleic acid end or the identifier having a phosphorylated end while the other is unphosphorylated for ligation. Single stranded ligation may also be employed.

Photo ligation may also be employed. Photo ligation may, for example, include covalently linking adjacent nucleic acids by application of electromagnetic energy, such as ultraviolet or visible light. Coupling agents may also be utilized to facilitate the formation of covalent linkages.

In some embodiments, dyes may be included into the identifiers. In one aspect, the identifiers may be doped with dyes. In another aspect, the identifier solutions may be mixed with dyes. According to one embodiment, the dyes may be photosensitive and may be fluorescent. According to another embodiment, the dyes maybe photosensitive and may be phosphorescent.

The substrates used may be glass, ceramic or polymeric, as long as their surfaces promote adhesion between the substrates and the targets. Polymers may include synthetic polymers as well as purified biological polymers. The substrate may also be any film, which may be non-porous or macroporous.

The substrate may be generally planar and may be of any appropriate geometry such as, for example, rectangular, square, circular, elliptical, triangular, other polygonal shape, irregular and/or any other appropriate geometry. The substrate may also be of other forms, such as cylindrical, spherical, irregular and/or any other appropriate form.

Appropriate ceramics may include, for example, hydroxyapatite, alumina, graphite and pyrolytic carbon.

Appropriate synthetic materials may include polymers such as polyamides (e.g., nylon), polyesters, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, ethylene vinyl acetates, polysulfones, nitrocelluloses and similar copolymers. These synthetic polymers may be woven or knitted into a mesh to form a matrix or similar structure. Alternatively, the synthetic polymer materials can be molded or cast into appropriate forms.

Biological polymers may be naturally occurring or produced in vitro by fermentation and the like or by recombinant genetic engineering. Recombinant DNA technology can be used to engineer virtually any polypeptide sequence and then amplify and express the protein in either bacterial or mammalian cells. Purified biological polymers can be appropriately formed into a substrate by techniques such as weaving, knitting, casting, molding, extrusion, cellular alignment and magnetic alignment. Suitable biological polymers include, without limitation, collagen, elastin, silk, keratin, gelatin, polyamino acids, polysaccharides (e.g., cellulose and starch) and copolymers thereof.

Any suitable substrate may be susceptible to adhesion, attachment or adsorption by targets. The susceptibility may be inherent or modified. In one example, the surfaces of substrates may be susceptible to adhesion, attachment or adsorption to proteins. In another example, the surfaces of substrates may be susceptible to adhesion, attachment or adsorption to proteins and not to nucleic acids.

In one exemplary embodiment, a glass substrate may have a layer or coating of a material that promotes adhesion with targets, such as proteins, materials that maybe charged, such as those that are positively charged, for binding target materials. Examples of charged materials include cellulosic materials, for example, nitrocellulose, methylcelluose, ethylcellulose, carboxymethyl cellulose, hydroxyethyl cellulose, methylhydroxypropyl cellulose; epoxies, PVDF (polyvinylidene fluoride); partially or fully hydrolyzed poly(vinyl alcohol); poly(vinylpyrrolidone); poly(ethyloxazoline); poly(ethylene oxide)-co-poly(propylene oxide) block copolymers; polyamines; polyacrylamide; hydroxypropylmethacrylate; polysucrose; hyaluronic acid; alginate; chitosan; dextran; gelatin and mixtures and copolymers thereof.

In another exemplary embodiment, if the substrate is not susceptible for attachment by charged materials, or may be susceptible only for attachment by wrongly charged materials, some areas of the substrate may have adhesives, binding agents, or similar attached, adsorbed or coated thereon. Examples of adhesives may include any suitable adhesives that bind the charged materials.

The targets may be present on the substrate discretely or in clusters. The distance between the discrete targets may be close or may be far apart and may usually be of different targets. Clusters may be used for multiple spots of a single target.

In one embodiment, the substrate may be macroporous. Macroporous substrates may be desirable, for example, if the different targets are very close together. When the targets are close by, there may not be sufficient distance between different targets to distinguish which target a biomolecule may be binding to. Closely packed targets may increase the efficiency of the generating of biomolecules. A macroporous substrate may be suited for balancing between efficiency and separation. For a macroporous substrate, the walls of the pores may be sufficient to separate even closely packed targets if the pores are large enough to enable the binding process to occur within the pores.

Also, for macroporous substrates, the pores may have an average diameter greater than the average size of the target material such that the target material may enter or partly enter the pores to anchor. Hydrogels may also be useful for binding or anchoring targets to the pores. Hydrogels may also fill the pores under fluid conditions and present a smooth surface for fluid flow while at the same time may keep the fluid from flowing through the pores.

The plurality of targets may be arranged in any appropriate manner such as, for example, in circular or elliptical spots, square or rectangular spots, stripes, concentric rings and/or any other appropriate arrangement on the subject.

According to one exemplary embodiment, the substrate may be at ambient temperature throughout.

According to another exemplary embodiment, the substrate may include a temperature affecting system that generally produces at least one desired temperature on the surface of the substrate and the adjacent fluid. The desired temperature may facilitate the biomolecule generating process.

According to a further exemplary embodiment, the substrate may include a temperature affecting system for producing a range of desired temperatures on the surface of the substrate and the adjacent fluid. This may be particularly useful when employing a set of targets having a significant range of, for example Tms, or melting temperatures. In one embodiment, the system may include a plurality of temperature affecting devices that are in thermal communication with the substrate. The plurality of devices may generally be disposed such that they may each produce a desired temperature in a given locality on the surface of the substrate. The set of targets may also be distributed on the surface of the substrate such that the temperature at the location of a target is substantially at the Tm of the target.

Temperature affecting devices may be any appropriate device that may substantially produce a desired temperature on a substrate and may include, but are not limited to, thermoelectric devices such as Peltier junction devices, semiconductor heating devices, resistive heating devices, inductive heating devices, heating/cooling pumps, electromagnetic radiation sources and/or any other appropriate devices. Temperature may also be affected by other systems, such as, for example, fluid flows including, but not limited to, water flows, air flows, and/or any other appropriate fluid flows.

In an exemplary embodiment, a plurality of Peltier junction devices may be utilized to generate desired temperatures at localities on the surface of the substrate. Peltier junction devices are particularly useful since they are able to both heat and cool using electrical current. This enables Peltier junction devices to generate temperatures above and below the ambient temperature of a system. They may also be useful in maintaining given temperature conditions at a steady state by adding and removing heat as necessary from the system.

In general, the placement of the temperature affecting devices may determine the temperature profile on the surface of the substrate and the adjacent fluid in the chamber. The temperature affecting devices may thus be disposed at appropriate positions such that given temperatures may be produced and maintained at known positions on the substrate.

The substrate may in general have a given thermal conductivity such that the application of at least one temperature affecting device may substantially generate a temperature gradient profile on the surface of the substrate. In general, the temperature on the surface of the substrate may change as a function of the distance from the position of the at least one temperature affecting device. Substrate materials with a relatively low thermal conductivity may generally produce highly localized temperature variations around a temperature affecting device. Substrate materials with a relatively high thermal conductivity may generally produce more gradual variations in temperature over a given distance from a temperature affecting device. It may be understood that at steady state, the effect of the thermal conductivity of the substrate may not contribute to the temperature profile of the system.

In some embodiments, at least one temperature affecting device may be utilized to produce a particular temperature gradient profile on the surface of the substrate. In general, a temperature gradient may be generated by utilizing at least one temperature affecting device producing a temperature different from the ambient temperature of the system. Multiple temperature affecting devices with at least two producing different temperatures may be utilized to generate a temperature gradient without reliance on the ambient temperature of the system.

The positions and temperatures of multiple temperature affecting devices may be utilized to calculate a resulting temperature gradient profile on the surface of a substrate using standard heat transfer equations. An algorithm may then be utilized to calculate the optimal positions and/or temperatures for a plurality of temperature affecting devices to produce a desired temperature gradient profile on the surface of a substrate. The algorithm may be, for example, applied using a computational assisting system, such as a computer and or other calculatory device. This may be performed to tailor a temperature gradient profile to a particular substrate with a known disposition of targets of known and/or calculated Tm. Similarly, a set of targets of known and/or calculated Tm may be arranged on a substrate based on a temperature gradient profile. This may be desirable as placement of a target at a given location on a substrate may be accomplished more easily than tailoring a temperature profile to pre-existing locations of targets on a substrate. In general, a target may be disposed on the substrate at a temperature address within the temperature profile gradient. The temperature address may, for example, be substantially at the Tm of the target during operation of the molecular hybridization system, and/or any other appropriate temperature.

In another aspect, the molecular hybridization system includes an adjustable system for generating a temperature profile. The adjustable system generally includes a plurality of temperature affecting devices, each affecting the temperature at a particular location of a substrate.

Details of the temperature affecting systems may be found in, for example, U.S. utility patent application Ser. No. 12/249,525, filed on Oct. 10, 2008, entitled "METHODS AND DEVICES FOR MOLECULAR ASSOCIATION AND IMAGING", the contents of all of which are hereby incorporated by reference.

Figure 6:
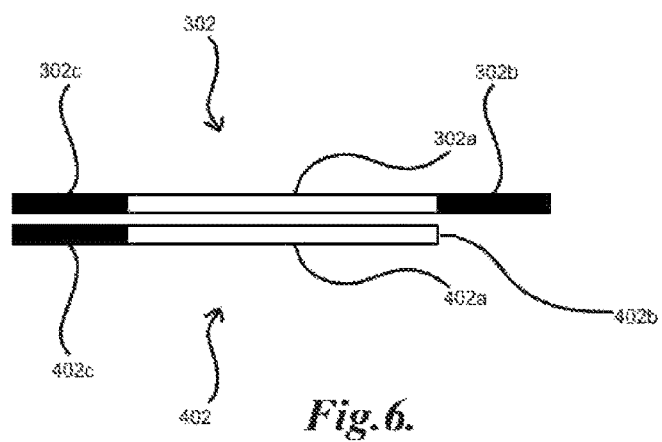
Figure 6A:
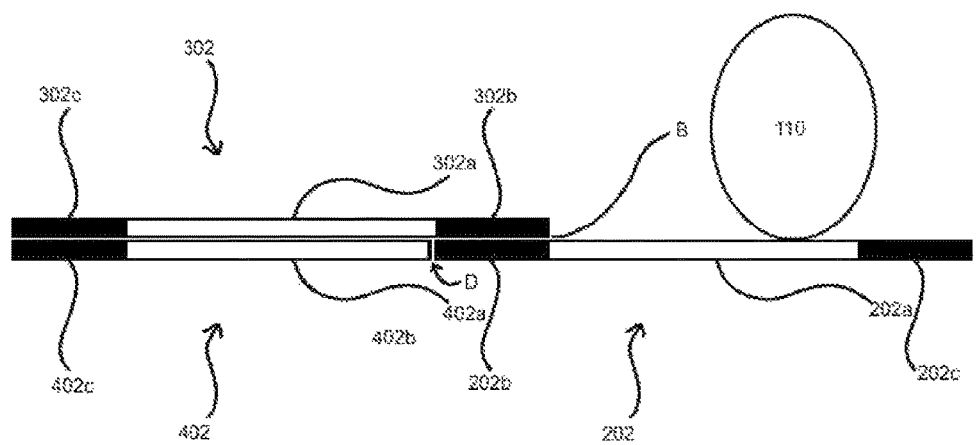
Figure 6B:
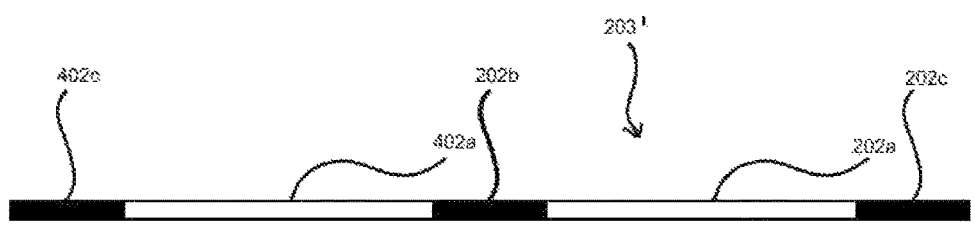

FIG. 6 illustrates an example of an identifier sequence 302 and a complement identifier sequence 402. The complement sequence 402 may include a complement identifier region 402a which may be substantially complementary to identifier region 302a such that they may base pair bind. The complement sequence 402 may further include a primer region 402c which may also be complementary to primer region 302c of the identifier 302. Further, the complement sequence 402 may include a compatible end 402b which may be compatible with ligation to the end of another nucleic acid. As shown in FIG. 6a, a nucleic acid library member 202 may be bound to a spot 110. An identifier 302 and a complement sequence 402 may then be applied to the member 202 such that the identifier 302 binds to the member 202 at region 202b, 302b. The complement sequence 402 may bind to the identifier 302 at regions 302a/402a, 302c/402c. The compatible end 402b may then be ligated to the end D of the member 202 by an appropriate ligase and/or other appropriate method. A product 203', as illustrated in FIG. 6b, may then be generated including the primer region 202c, binding sequence 202a, region 202b, complement identifier region 402a, and complement primer region 402c. The product 203' may then be amplified, such as with the product 203 discussed above in FIG. 4a. The product 203' may also be generated by single-stranded ligation of the member 202 and the complement sequence 402, where in general the either the member 202 or the complement sequence 402 may have a phosphorylated end while the other may be unphosphorylated for end to end ligation.

In another example, as illustrated in FIG. 6c, a further complementary fragment 502 may be included that may base pair bind to a complementary region 202d of the nucleic acid library member 202. This may be desirable as some nucleic acid ligases may generally join double stranded nucleic acids. The addition of the complementary fragment 502 may generally generate a substantially double stranded nucleic acid, such as illustrated spanning from region 302c to the end of complementary fragment 502. There may further be a double stranded "break" at points D and E. In general, the sizing of the fragments may be tailored to generate a suitably long stretch of double stranded nucleic acid for ligase action. In general, the complementary region 202d may be the same for all members 202 of the library 200 such that the same complementary fragment 502 may be utilized, such as, for example, convenience, cost and/or ease of use.

In general, methods may be applied that may facilitate binding or other interactions between the identifiers and the nucleic acids bound to the spots. For example, the temperature may be increased to dissociate the nucleic acids from the spots. The temperature may subsequently be lowered such that, for example, base pairing may occur between the nucleic acids and the identifiers. Temperature changes may also, for example, denature the target such that the nucleic acids may no longer bind and/or bind with lower affinity to the targets. This may be desirable in that it may aid in binding of the nucleic acids to the identifiers.

In a further aspect of the invention, methods for monitoring and/or controlling the diversity of the library of biomolecules may be utilized. For example, too few rounds of selection may result in a biomolecule pool with too many weak binding members while too many rounds of selection may result in only a few binding members, such as members corresponding to only a few targets rather than members corresponding to all of the targets present. In one embodiment, Cot analysis may be employed to measure and/or monitor the diversity of the library of biomolecules through multiple rounds of selection. Cot, or Concentration×time, analysis measures the annealing time of particular oligonucleotides while in solution with other nucleic acids, such as the members of the library of biomolecules. In general, the annealing time will be faster the lower the diversity of the library.

In one embodiment, a Cot-standard curve for measuring the sequence diversity of the aptamer library at any point during the multiplex SELEX process may be utilized. For example, a group of DNA oligonucleotides with a 5'- and 3'-constant region of ~20 bases identical to the initial SELEX library may be utilized. The oligos may then be converted to dsDNA by standard methods. Briefly, after annealing a primer to the oligos, Exo-minus Klenow Taq polymerase (Epicentre, Madison, Wis.) may be used in conjunction with dNTPs to fill in the ssDNA to create a dsDNA or mixture thereof. Using a standard quantitative PCR thermal cycler, a temperature profile for melting and controlled annealing of each DNA mixture may be programmed. Standard SYBR Green I specific for double-stranded DNA (dsDNA) may be utilized to report the amount of re-annealed dsDNA. At one extreme, the annealing time for a single sequence will be measured. At the other extreme, the annealing time for the initial SELEX pool, such as containing approximately 1 nmol of sequence diversity, may be measured. Annealing times of intermediate diversity may also be measured to establish a very specific Cot-standard-curve for the SELEX library. Using this standard curve, at any point during SELEX, the sequence diversity of the evolving library of aptamers may be determined by comparison to the curve.

In a further embodiment, a method for generating functional biomolecules includes obtaining a library of peptide sequences and contacting the library with a plurality of targets. In some embodiments, the peptide sequence may be tagged, linked, marked and/or otherwise associated with a nucleic acid sequence. The nucleic acid sequence may be, for example, representative of the sequence of the peptide. For example, the nucleic acid may substantially encode the peptide sequence. Also for example, the nucleic acid may be a unique or semi-unique identifier sequence. The nucleic acid sequence may then be utilized to bind another identifier, as described above, such that a peptide bound to a target may be tagged or marked as to which target it bound.

In an exemplary embodiment, a bacteriophage (phage) may be generated that includes a peptide sequence of interest in its protein coat. The phage may further include a nucleic acid sequence that may be representative of the peptide sequence within the nucleic acid of the phage. The phage may then be contacted with a plurality of targets, as above. This may generally be referred to as phage display. Phages employed may include, but are not limited to, M13 phage, fd filamentous phage, T4 phage, T7 phage, λ phage, and/or any other appropriate phage. Non-binding phages may be washed and/or partitioned, while binding phages may be tagged or marked with identifiers, as above. As phage nucleic acids are generally contained within the protein coat of the phage, the nucleic acid may generally be exposed for binding to the identifier. For example, the phage may be heated such that the protein coat denatures and/or disassembles such that the nucleic acid is exposed. The identifier may also be introduced into the phage, such as by electroporation, electrophoresis, and/or any other appropriate method.

In FIG. 7, an example of a phage 600 may include a nucleic acid 610 which may generally encode, among other things, and be encapsulated by a protein coat 602, which may contain a binding region for a target 110. The nucleic acid 610 may further include a region 612 which may identify the phage and/or encode the binding region for a target. A bound phage 600, as illustrated in FIGS. 7 and 7a, may then be heated, disrupted and/or otherwise treated such that an identifier 302 may contact F the region 612. For example, the protein coat 602 may be broken and/or otherwise disrupted for entry of the identifier 302. In general, an amplification reaction and/or other method, such as those discussed above, may be utilized to tag, mark and/or otherwise introduce identifier information to the sequence of region 612. Further in general, the identifier 302 and region 612 may incorporate any, all or a combination of the elements discussed above in regards to nucleic acid library members, identifiers and/or other nucleic acid fragments. As also discussed above, the phage 600 may also be physically removed and/or partitioned in a manner that may preserve the identity of the target 110 the phage 600 was associated.

In other embodiments, other methods of incorporating and/or linking nucleic acids to peptides may be utilized, such as, for example, mRNA display, ribosome display, and/or any other appropriate method. In general, in mRNA display, as illustrated in FIG. 7b, a fusion product 600' of a messenger RNA (mRNA) 610' may be linked to a peptide 602' that the mRNA 610' encodes, such as with a puromycin-ended mRNA 612' which may generally cause fusion of the mRNA 610' to the nascent peptide 602' in a ribosome, which may then be contacted with targets such as described above with phage display. Also in general, in ribosome display, as illustrated in FIG. 7c, a fusion product 600" of a modified mRNA 610" may be utilized that codes for a peptide 602", but lacks a stop codon and may also incorporate a spacer sequence 612" which may occupy the channel of the ribosome 620" during translation and allow the peptide 602" assembled at the ribosome 620" to fold, which may result in the peptide 602" attached to the ribosome 620" and also attached to the mRNA 610". This product 600" may then be contacted with targets such as described above with phage display. Other methods may include, but are not limited to, yeast display, bacterial display, and/or any other appropriate method.

In another aspect of the invention, methods for handling and sorting the resultant sequences of a multiplexed binding process are provided. In some embodiments, the sequences may be sorted by identifier sequences to establish which target or targets the sequence bound. The sequences may further be compared, aligned and/or otherwise processed to identify features, characteristics and/or other useful properties, relationships to each other, and/or target properties. For example, it may be expected that multiple aptamer sequences bound to a single target may potentially share sequence motifs and/or other common features which may be at least partially elucidated by sequence sorting and/or comparison. Specific binding affinities of resultant sequences may also be determined through affinity assays. In some embodiments, surface plasmon resonance may be utilized to determine binding of an aptamer to a target. For example, sensors which monitor the refractive index of a surface bound to a target may be utilized, where the refractive index may change as a result of binding of an aptamer to the target. In general, aside from standard sequencing methods, parallel sequencing methods, such as, for example, massively parallel sequencing such as 454 Clonal Sequencing (Roche, Branford, Conn.), massively parallel clonal array sequencing, Solexa Sequencing (Illumina, San Diego, Calif.), and/or any other appropriate sequencing method may be employed.

Figure 9:
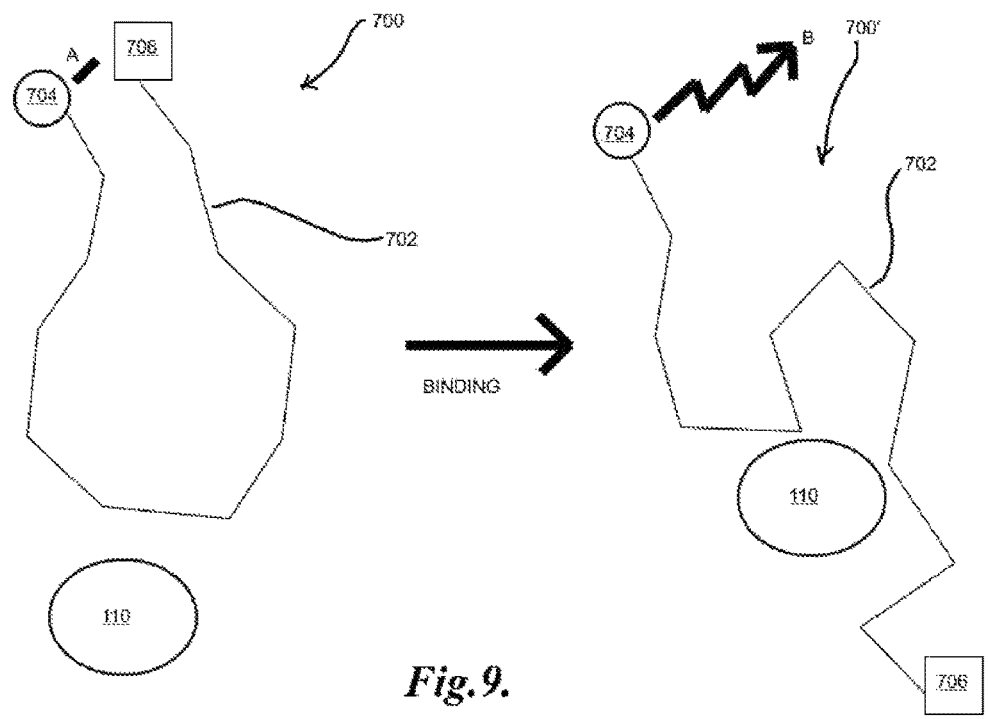
FIG. 9 illustrates an example of binding of an aptamer beacon to a target molecule.

Aptamers may also be utilized to create molecular beacons which may fluoresce and/or otherwise produce a detectable signal when the aptamer binds to its target. Aptamers typically undergo a conformational change when binding a target and this conformational change may be utilized to modulate the activity of other molecules or components of a molecule, such as modulating the distance between a fluorophore (fluor) and a quencher. In general, an aptamer beacon may include an aptamer with a fluor and a quencher attached to the 5' and 3' ends, respectively, or vice versa. The aptamer in its unbound state may generally be designed to keep the fluor and quencher in proximity such that quenching of the fluor occurs and thus little or no fluorescent signal produced. Linkers and/or stem structures may also be utilized with the base aptamer to produce this quenching effect in the unbound state. Such linkers and/or stem structures to produce "beacon" structures in nucleic acids are generally well known and are standard laboratory techniques. When the aptamer binds to its target, its conformational change upon binding may then generally cause spacing of the fluor and quencher such that the fluor may undergo fluorescence without quenching by the quencher, and such fluorescence may then be detected as a signal to indicate binding of the target to the aptamer. FIG. 9 illustrates the conformational changes of an unbound aptamer beacon structure 700 when binding to a target molecule 110 at the aptamer portion 702, showing the fluor 704 and quencher 706 in an initial proximity resulting in quenching A and a fluorescence emitting B conformation after binding the target molecule 110 to yield bound conformation 700'.

Aptamers may also be selected and/or designed to exhibit large, detectable and/or specific switching conformational changes when binding to a target molecule. In general, aptamers frequently exhibit induced-fit folding behavior, where the aptamer may be largely unstructured in solution and may undergo significant compaction and/or structural stabilization upon binding its target molecule. In some embodiments, aptamers may be selected and/or designed such that a portion of the aptamer may hybridize to another nucleic acid, such as a primer, anchoring oligo and/or other nucleic acid with a complementary sequence, and may dehybridize from such nucleic acid when the aptamer binds to its target molecule, such as to release the aptamer from such hybridized nucleic acid.

Example of Multiplexed Selex Protocol

As a demonstration of parallel, de novo selection of aptamers against multiple targets, a combinatorial DNA library containing a core randomized sequence of 40 nts flanked by two 20 nt conserved primer binding sites is used as the starting point for an aptamer pool. The primer sequences are designed and optimized using Vector NTI's (Invitrogen) oligo analysis module. Typically, such a library is expected to contain approximately $10^{15}$ unique sequences. The primer binding sites are used to amplify the core sequences during the SELEX process. The single stranded DNA pool dissolved in binding buffer is denatured by heating at 95° C. for 5 min, cooled on ice for 10 min and exposed to multiple protein targets fixed onto a nitrocellulose coated glass slide (e.g., Whatman).

Example of Dna Library Selex

An example DNA library consists of a random sequence of 40 nucleotides flanked by conserved primers. In the first round of SELEX, 500 pmol of the ssDNA pool is incubated with each slide in binding buffer (PBS with 0.1 mg/ml yeast tRNA and 1 mg/ml BSA) for 30 minutes at 37° C. The slide is then washed in 1 ml of binding buffer for one minute. To elute specifically bound aptamers the slide is heated to 95° C. in binding buffer. The eluted ssDNA is subsequently be precipitated using a high salt solution and ethanol. After precipitation, the aptamer pellet is resuspended in water and amplified by PCR with a 3'-biotin-labeled primer and a 5'-fluorescein (FITC)-labeled primer (20 cycles of 30 sec at 95° C., 30 sec at 52° C., and 30 sec at 72° C., followed by a 10 min extension at 72° C.). The selected FITC-labeled sense ssDNA is separated from the biotinylated antisense ssDNA by streptavidin-coated Sepharose beads (Promega, Madison, Wis.) for use in the next round. Alternatively, "asymmetric PCR" may be utilized for generating a large excess of an intended strand of a PCR product in SELEX procedures. Also alternatively, the undesired strand may be digested by λ-exonuclease, such as, for example, when a phosphorylated PCR primer is employed.

The labeling of individual aptamers with fluorescein isothiocyanate (FITC) facilitates the monitoring of the SELEX procedure. FITC is also compatible with scanning in the green (cy3) channel of standard microarray scanners. The sense primer used to amplify the ssDNA aptamers after each round of selection is fluorescently labeled, resulting in fluorescently labeled aptamers. The protein spotted nitrocellulose-coated slides are scanned in a microarray scanner. Alternatively, proteins may be spotted on epoxy-coated glass slides. While epoxy slides may have less protein binding capacity than 3-D nitrocellulose pads, it has been observed that there may be less non-specific binding of nucleic acid aptamer pools to the background of the slide (blocked or not). Blocking may be employed to reduce background fluorescence.

In each round of the SELEX process, the slide is incubated for 30 min at 37° C. to allow binding of the aptamers to their targets. The slides are then washed in binding buffer before the specifically bound DNAs are eluted by heating the slide at 95° C. in 7M urea. Nucleic acids from the eluate are phenol-chloroform purified and precipitated, and the concentrated single stranded DNA molecules will be amplified by PCR. In order to increase stringency throughout the SELEX process, the washes are gradually increased in volume (from approximately 1-10 ml). After a given point in the selection, such as, for example, after the final round of selection, the aptamers may be tagged, marked and/or partitioned.

Example of In Situ Hybridization of Identifiers

An example of in situ hybridization of identifiers to aptamers was performed with short, ssDNA sequence tags to the 3' end of aptamers bound to their protein target. These synthetic ssDNA tag oligonucleotides consists of three regions, as illustrated in FIG. 3b with identifier 302: (i) the C2 region, region 302c of the identifier 302, at the 3' end of the oligonucleotide consists of a 17-20 nucleotide sequence complementary to a corresponding region on all of the used aptamers, (ii) the C1 region, region 302b at the 5' end of the oligonucleotide 302 contains a 17-20 nt primer binding site, used during the amplification of the tag:aptamer hybrid, prior to sequencing and (iii) a variable region 302a in the center of the tag oligonucleotide (V) that serves a as a unique identifier for each locus on the glass slide surface. A variable sequence of 8 nucleotides will allow 48 (65,536) unique sequences to be generated, sufficient for many complex protein arrays (8000 samples) on the market.

As outlined above, after the final round of the SELEX procedure (typically, round 10) the specific aptamers are bound to their protein targets, fixed to a glass slide. While the 40 nt core sequence of each aptamer are unique, its terminal sequences have not been subject to any kind of selection during the procedure. After each round of binding to their protein targets, the aptamers were amplified using conserved primers, requiring the maintenance of corresponding regions at their distal ends (P1, P2). The 3'-region of each aptamer, for instance, can thus serve as a binding site (via standard hybridization) for the C2 region of the proposed tag oligonucleotide. Given the unique variable sequence (V) of each tag oligonucleotide, each aptamer will now be tagged with a sequence that can be traced back to the location of the aptamer on the glass slide, and thus the protein spotted at that location.

Example Of Selex Against Targets

A SELEX procedure as described above was performed utilizing target molecules such as amino acids, such as citrulline, and to target molecules such as crystallin or its subunits, such as alpha crystallin B-chain (CRYAB), to produce candidate aptamers, and to yield aptamer sequences given in the sequence listing above. The sequences yielded are artificial, non-naturally occurring sequences designed and/or selected for artificially for specific and/or high affinity binding to utilizing opioids and/or opioid metabolites and/or similar/related molecules, where the sequences have no known natural function. Any of the sequences, such as SEQ IDs 1-230, may also have SEQ ID 231 and/or 232 appended to either the 5'-end, 3'-end, or both ends, interchangeably, such as to, for example and without limitation, provide priming sequences, anchoring sequences (e.g. via hybridization), and/or conformational structure switching behavior (e.g. via switching between hybridized to a nucleic acid and unhybridized while bound to a target molecule), yielding aptamers with the general structures: 5'-Seq231-SeqX-Seq232-3', 5'-Seq232-SeqX-Seq70-231', 5'-Seq231-SeqX-3', 5'-Seq232-SeqX-3', 5'-SeqX-Seq231-3' and 5'-SeqX-Seq232-3', where SeqX denotes one of SEQ IDs 1-230.

It will be appreciated by those of ordinary skill in the art that the present invention can be embodied in other specific forms without departing from the spirit or essential character hereof. The present description is therefore considered in all respects to be illustrative and not restrictive. The scope of the present invention is indicated by the appended claims, and all changes that come within the meaning and range of equivalents thereof are intended to be embraced therein.

The invention claimed is:

1. An artificial ligand binding to citrulline comprising a non-naturally occurring nucleic acid sequence of under 40 nucleotides in length having substantial homology and greater than 80% sequence identity to a sequence selected from the group consisting of SEQ IDs 2-10.

2. The artificial ligand of claim 1 wherein at least one nucleotide is substituted with a non-natural analog.

3. The artificial ligand of claim 1 further comprising an appended 5'-sequence selected from the group consisting of SEQ IDs 231-232.

4. The artificial ligand of claim 1 further comprising an appended 3'-sequence selected from the group consisting of SEQ IDs 231-232.

5. The artificial ligand of claim 1 further comprising an appended 5'-sequence and an appended 3'-sequence selected from the group consisting of SEQ IDs 231-232.

6. An artificial ligand binding to citrulline consisting essentially of a non-naturally occurring nucleic acid sequence having the sequence selected from the group consisting of SEQ IDs 1-10.

7. The artificial ligand of claim 6 wherein at least one nucleotide is substituted with a non-natural analog.

8. The artificial ligand of claim 6 wherein said non-naturally occurring nucleic acid sequence is appended with a 5'-sequence selected from the group consisting of SEQ IDs 231-232.

9. The artificial ligand of claim 6 wherein said non-naturally occurring nucleic acid sequence is appended with a 3'-sequence selected from the group consisting of SEQ IDs 231-232.

10. The artificial ligand of claim 6 wherein said non-naturally occurring nucleic acid sequence is appended with a 5'-sequence and a 3'-sequence selected from the group consisting of SEQ IDs 231-232.

* * * * *

SEQUENCE LISTING

```
<160> NUMBER OF SEQ ID NOS: 332

<210> SEQ ID NO 1
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 1 taggggggcgg ggccgatgac accaggcgct tt                                    32

<210> SEQ ID NO 2
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 2
cttggacgta catatgacct gattcgacgg gg                                     32

<210> SEQ ID NO 3
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 3
ggtcgcgttt ttatagacct gcattggcat tg                                     32

<210> SEQ ID NO 4
<211> LENGTH: 32
```

```
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 4
ggtcgcgttt ttatgacctg catcggcatt gg                                       32

<210> SEQ ID NO 5
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 5
tagacagggt gagggatta tgaccgtcat tc                                        32

<210> SEQ ID NO 6
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 6
tacgctagag tgtgtgatca ggcgtagtcc gt                                       32

<210> SEQ ID NO 7
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 7
tacggaagag gcatattatg acctagcgtc gt                                       32

<210> SEQ ID NO 8
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 8
ggacactagg aatctacctg acgtgcgtgg gg                                       32

<210> SEQ ID NO 9
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 9
ggtcgcgttt tatgaccttg cattggcatt gg                                       32

<210> SEQ ID NO 10
<211> LENGTH: 32
<212> TYPE: DNA
```

```
<213> ORGANISM: Artificial Sequence
<220> FEATURE:
<223> OTHER INFORMATION: Non-naturally occuring artificial aptamer
      sequence binding to a target molecule.

<400> SEQUENCE: 10
gtgatcgtgg tatgacctga cgcatagaca ct                                    32

<210> SEQ ID NO 11
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 11
tacgagaggc agctattatg acctacgcgc at                                    32

<210> SEQ ID NO 12
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 12
taggtatgag ccaaaaccac agtgcgagtg ga                                    32

<210> SEQ ID NO 13
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 13
tgacagtaag acctgtattc gctgtagatt gc                                    32

<210> SEQ ID NO 14
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 14
gctgggaggt cacagttggt gcgaaagcct ga                                    32

<210> SEQ ID NO 15
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 15
ggtcgcgttt ttagtgacct gcattggcat tg                                    32

<210> SEQ ID NO 16
<211> LENGTH: 32
<212> TYPE: DNA
<213> ORGANISM: Artificial Sequence
```

```
<220> FEATURE:
<223> OTHER INFORMATION: Non-naturally occuring artificial aptamer
      sequence binding to a target molecule.

<400> SEQUENCE: 16
ggtcgcgttt ttatgaccag cattggcatt gg                                    32

<210> SEQ ID NO 17
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 17
ggtcacgttt tcatgacctg tattagcatt gg                                    32

<210> SEQ ID NO 18
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 18
gtgagggcaa aatgacctga ttccagtgct tc                                    32

<210> SEQ ID NO 19
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 19
tagtgactga ttcggactga cgacagctac tc                                    32

<210> SEQ ID NO 20
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 20
tgatcgtggt atgacctgac ggcatagaca ct                                    32

<210> SEQ ID NO 21
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 21
cttggacgta catatgacct gatttcgcgg gg                                    32

<210> SEQ ID NO 22
<211> LENGTH: 32
<212> TYPE: DNA
<213> ORGANISM: Artificial Sequence
<220> FEATURE:
```

```
<223> OTHER INFORMATION: Non-naturally occuring artificial aptamer
      sequence binding to a target molecule.

<400> SEQUENCE: 22
gaaccaagtc cgagacgaga aggccaaacg ga                                      32

<210> SEQ ID NO 23
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 23
gcggaacgcg gtgtatgtga cctgattcgc tc                                      32

<210> SEQ ID NO 24
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 24
ggtcgaccgg caatcagtac gcggtgatgt aa                                      32

<210> SEQ ID NO 25
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 25
gtgcaccgca tccggactaa gacaaggcca ac                                      32

<210> SEQ ID NO 26
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 26
tagaaaacca caacatagcg ccattgcgga tt                                      32

<210> SEQ ID NO 27
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 27
tacatgaagt tacacacggg cgaccgtctc ac                                      32

<210> SEQ ID NO 28
<211> LENGTH: 32
<212> TYPE: DNA
<213> ORGANISM: Artificial Sequence
<220> FEATURE:
<223> OTHER INFORMATION: Non-naturally occuring artificial aptamer
```

-continued sequence binding to a target molecule.

<400> SEQUENCE: 28
tacgagtgtt taacgtgcgg aagattcgac tc                                32

<210> SEQ ID NO 29
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 29
tgtagagtta cgcatgacct ggattcgcgg ac                                32

<210> SEQ ID NO 30
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 30
tgtaggcaac aagtacgaat gacctgattc gc                                32

<210> SEQ ID NO 31
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 31
cgcgaccaaa tcattttgac ctggattcgt ac                                32

<210> SEQ ID NO 32
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 32
gaaacagatg tcggcaagga caatggcacc aa                                32

<210> SEQ ID NO 33
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 33
gaggggacaa cttgcactcg ggcgtgcgta cg                                32

<210> SEQ ID NO 34
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 34
gcttaggcgg attatgacct tgaggaagca ta                    32

<210> SEQ ID NO 35
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 35
ggaccagtcc gcgtgttcgt aagggagtgc ta                    32

<210> SEQ ID NO 36
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 36
ggtccgctgt agatgacctg attcgcgcgc ca                    32

<210> SEQ ID NO 37
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 37
ggtcgcgttt tatgacctgc attggccatt gg                    32

<210> SEQ ID NO 38
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 38
ggtcgcgttt ttatgacctg cattggcact gg                    32

<210> SEQ ID NO 39
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 39
ggtgacctga tccgaagtgg cgcacggaga aa                    32

<210> SEQ ID NO 40
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 40
ggtgacctga ttcggatgac gacaagttac tc                                    32

<210> SEQ ID NO 41
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 41
gggtagcgta gatgacctga acattcgcca ca                                    32

<210> SEQ ID NO 42
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 42
ggtcacgctt ttcatgacct gcattagctt gg                                    32

<210> SEQ ID NO 43
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 43
tacgatgcac acaagatgtg gagcaggaag tg                                    32

<210> SEQ ID NO 44
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 44
tacgtgcaca gctagtgggg ctgacctgat tc                                    32

<210> SEQ ID NO 45
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 45
tgagtcgtgg tatgacctga cgcatagaca ct                                    32

<210> SEQ ID NO 46
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 46
tgatcgtggt atgacctgac gcaatagaca ct          32

<210> SEQ ID NO 47
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 47
tgggggtgac ctgccaactg cattcgcggg aa          32

<210> SEQ ID NO 48
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 48
tgtgaccgtg atcggattgt gagagactcg at          32

<210> SEQ ID NO 49
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 49
tgtggagttg acctgtgaac gcataggcat gt          32

<210> SEQ ID NO 50
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 50
tgtggagtta cgcatgacct ggattcgcgg ac          32

<210> SEQ ID NO 51
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 51
taggaagggg ttgggtggga gggtattggc ta          32

<210> SEQ ID NO 52
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 52
aggaggtggt gacctgattc gcgagactcg ta                                    32

<210> SEQ ID NO 53
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 53
aggaggtggt gacctggatt cgcgagatcg ta                                    32

<210> SEQ ID NO 54
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 54
aggatacaat gacctgattc cagttggcct at                                    32

<210> SEQ ID NO 55
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 55
aggatgcaat cgacctgatt ccgttggccc at                                    32

<210> SEQ ID NO 56
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 56
attacgtgca cgctagtggg ctgacctgat tc                                    32

<210> SEQ ID NO 57
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 57
ccgatcgtgg tatgacctga cgcatagaca ct                                    32

<210> SEQ ID NO 58
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 58
cgtagtcccg ggaagcgtga cctgattcgc ct                                    32

<210> SEQ ID NO 59
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 59
ctcatacggt agtgggaggg gggcgatcca at                                    32

<210> SEQ ID NO 60
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 60
cgttgaaatg acctgattcg caatcacttg ct                                    32

<210> SEQ ID NO 61
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 61
ctgatcgtgg tatgacctga cgcatagata ct                                    32

<210> SEQ ID NO 62
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 62
ctggctgttg ttgcgggtag acactaggat ac                                    32

<210> SEQ ID NO 63
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 63
gaggatggca agtactgact tccgttggcc at                                    32

<210> SEQ ID NO 64
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 64
gaggggttct ttgacctgca ttcggagcat ca                                    32

<210> SEQ ID NO 65
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 65
gagggatgtg ccgaggtttc gtatagctcg tg                                    32

<210> SEQ ID NO 66
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 66
gctgttatga cccattcgct gtaacggcta ac                                    32

<210> SEQ ID NO 67
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 67
gcgcatcgta ttgactgtat cgacgtacgc at                                    32

<210> SEQ ID NO 68
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 68
gcgggtgtga cctgcattct cattgggggg at                                    32

<210> SEQ ID NO 69
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 69
gcgggaacgc agtgtatatg actgattcgc tc                                    32

<210> SEQ ID NO 70
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 70
gcgtagaaga cgtgactgcc atcatttgga tt                                    32

```
<210> SEQ ID NO 71
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 71
gcgtaagtgt aacgagaaca tgactgtgac ct                                    32

<210> SEQ ID NO 72
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 72
gcgtacctgc cgcggatgac ctgtatcgct gt                                    32

<210> SEQ ID NO 73
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 73
gcgtaggtgg gatggattat gacctgcatt ga                                    32

<210> SEQ ID NO 74
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 74
gcgtagtccg ggaacgtgac ctgacttcgc ct                                    32

<210> SEQ ID NO 75
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 75
gcgtgccact tgagggctga cctgattcgg at                                    32

<210> SEQ ID NO 76
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 76 gcgtggggc gaagagcgtt cacttcaacg ac                                     32

<210> SEQ ID NO 77
```

```
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 77
gcgttgggct agtgtgacct gattcgttgt ac                                     32

<210> SEQ ID NO 78
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 78
gctaagttgg agttgaccgt gatgagcggt gt                                     32

<210> SEQ ID NO 79
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 79
gctacctgcc gcggatgacc tatattcgct gt                                     32

<210> SEQ ID NO 80
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 80
gctagggatc cctattaatg gcgcttgctg gc                                     32

<210> SEQ ID NO 81
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 81
gctagtcccg ggaaacgtga cctgattcgc ct                                     32

<210> SEQ ID NO 82
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 82
gctatgtggg gatggattat gacctgcatt ga                                     32

<210> SEQ ID NO 83
<211> LENGTH: 32
```

<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 83
ggaacgggac gacctgacat tcgctaaatg tt                          32

<210> SEQ ID NO 84
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 84
ggacagcttg tctgccttgg aaagggttac tg                          32

<210> SEQ ID NO 85
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 85
ggacggactt tgtgttgcat aatgcgttat gg                          32

<210> SEQ ID NO 86
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 86
ggacgtagtc cggaacgtga cctgattcgc ct                          32

<210> SEQ ID NO 87
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 87
ggtcgccgtt tttatgacct gcattggcat tg                          32

<210> SEQ ID NO 88
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 88
ggtcgcgtct ttatgacctg cattggcatt gg                          32

<210> SEQ ID NO 89
<211> LENGTH: 32
<212> TYPE: DNA

<213> ORGANISM: Artificial Sequence
<220> FEATURE:
<223> OTHER INFORMATION: Non-naturally occuring artificial aptamer
      sequence binding to a target molecule.

<400> SEQUENCE: 89
ggtccgctgt agatgacctg attcgcgcgt ta                          32

<210> SEQ ID NO 90
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 90
ggtcgacgtt ttatgacctg cattggcatt gg                          32

<210> SEQ ID NO 91
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 91
ggtcgcagtt tttatgacct gcattggcat tg                          32

<210> SEQ ID NO 92
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 92
ggtcgcgttt tatgacctgc attggcattg gg                          32

<210> SEQ ID NO 93
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 93
ggtcgcgttt tatgacctgt cattggcatt gg                          32

<210> SEQ ID NO 94
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 94
ggtcgcgttt ttatgaccta cattggcatt gg                          32

<210> SEQ ID NO 95
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 95
ggtcgtgttt ttatgacctg cattggcatt gg                          32

<210> SEQ ID NO 96
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 96
gggtcgcgtt ttgatgacct gcattggcat tg                          32

<210> SEQ ID NO 97
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 97
ggtaacgttt tcatgacctg cattggcatt gg                          32

<210> SEQ ID NO 98
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 98
ggtacgatgc aatatcgata ttcgtcgtcg ca                          32

<210> SEQ ID NO 99
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 99
ggtagtatgg tggcttgcgg ccagaatatg tg                          32

<210> SEQ ID NO 100
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 100
ggtaggatat cgaatgacct gattcgctcc ta                          32

<210> SEQ ID NO 101
<211> LENGTH: 32
<212> TYPE: DNA
<213> ORGANISM: Artificial Sequence
<220> FEATURE:

<223> OTHER INFORMATION: Non-naturally occuring artificial aptamer
      sequence binding to a target molecule.

<400> SEQUENCE: 101
ggtcacgttt ttatgacctg cattagcatt gg                                32

<210> SEQ ID NO 102
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 102
gtaggcgtcg tatgacctga cattcgccac at                                32

<210> SEQ ID NO 103
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 103
gtgtagggtg tggatacggc ataggggggg ga                                32

<210> SEQ ID NO 104
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 104
tagacggcaa tgacctgatt ccgttggcct at                                32

<210> SEQ ID NO 105
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 105
tagcggatca acgcaggcag tggcagcatt tt                                32

<210> SEQ ID NO 106
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 106
tacaggagtc aaagggtcag ctatcgagcc gc                                32

<210> SEQ ID NO 107
<211> LENGTH: 32
<212> TYPE: DNA
<213> ORGANISM: Artificial Sequence
<220> FEATURE:
<223> OTHER INFORMATION: Non-naturally occuring artificial aptamer sequence binding to a target molecule.

<400> SEQUENCE: 107
tacgagacgg caactatctg actacgagtc gt                                    32

<210> SEQ ID NO 108
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 108
tagtatctat gacctgccta tccgctgtca ac                                    32

<210> SEQ ID NO 109
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 109
tagtccacaa atggcgacag gagtttcggg ca                                    32

<210> SEQ ID NO 110
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 110
tagtgactga ttcggatgac gacaggctac tc                                    32

<210> SEQ ID NO 111
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 111
tcctcgtctg aaacctcatt gtttaggtta gc                                    32

<210> SEQ ID NO 112
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 112
tcgtagtccg ggaaacgtga cctgattcgc ct                                    32

<210> SEQ ID NO 113
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

```
<400> SEQUENCE: 113
tgagaagctg tttgacattc cacggagcgc gc                                32

<210> SEQ ID NO 114
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 114
tggtgacctg attcggatga cgacagctac tc                                32

<210> SEQ ID NO 115
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 115
tgtaaggggg cggcaatcac cgtatggtct ga                                32

<210> SEQ ID NO 116
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 116
tgtagtaccg gaactgtgac ctgaattcgc ct                                32

<210> SEQ ID NO 117
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 117
tggcgaagtg tatcgtagag cgaaatggag ct                                32

<210> SEQ ID NO 118
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 118
tggggcgaaa cattcgctgg acgggacatc tc                                32

<210> SEQ ID NO 119
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.
```

```
<400> SEQUENCE: 119
tggtagttcc gggaacgtga cctgattcgc ct                          32

<210> SEQ ID NO 120
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 120
tggtagttcg tgaaactgtg acctgattcg ct                          32

<210> SEQ ID NO 121
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 121
tgtagttccg ggaaacggtg cctgattcgc ct                          32

<210> SEQ ID NO 122
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 122
tgtagttccg ggaaacgtga cctgatccgc ct                          32

<210> SEQ ID NO 123
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 123
tgtagttccg ggaaacgtga cctgattcac ct                          32

<210> SEQ ID NO 124
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 124
tgtgaccaaa tcttttggc ctgtattcgt ac                           32

<210> SEQ ID NO 125
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 125
```
tgtgaccaat cgttttggac ctgtattcgt ac					32

<210> SEQ ID NO 126
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 126
tgtgacctga tccggatgac gacaagtcac tc					32

<210> SEQ ID NO 127
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 127
tgtgacctga tccggattgt gagagacccg at					32

<210> SEQ ID NO 128
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 128
tgtgaccgtg attcgatgac gacaagttac tc					32

<210> SEQ ID NO 129
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 129
tgtgacctaa ttcggatgac gacaagttac tc					32

<210> SEQ ID NO 130
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 130
tgtgacctaa ttcggatgac gacaggctac tc					32

<210> SEQ ID NO 131
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 131

```
tgtgacctcg attcgatgag acaagagtac tc                            32
```

<210> SEQ ID NO 132
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 132

```
tgtgacctga ttcactttga gaccacagtg cc                            32
```

<210> SEQ ID NO 133
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 133

```
tgtgacctga ttcgatgacg acgtaggcta ct                            32
```

<210> SEQ ID NO 134
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 134

```
tgtgacctga ttcggaagac gacgagttgc tc                            32
```

<210> SEQ ID NO 135
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 135

```
tgtggccggg tagctaggtg gcgataggat tc                            32
```

<210> SEQ ID NO 136
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 136

```
aggacgtaga aatattcgct gggggaaccc ga                            32
```

<210> SEQ ID NO 137
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 137

```
agttagagat gacctgccgc agtcgtcaga ta                            32
```

```
<210> SEQ ID NO 138
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 138
aggagatatg acctgattcc tgtctgctgg ga                                    32

<210> SEQ ID NO 139
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 139
aggagatgtg acctgattcc tgtctactgg ga                                    32

<210> SEQ ID NO 140
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 140
aggactgcaa tgacctgatt ccgttggcct at                                    32

<210> SEQ ID NO 141
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 141
aggagatgtg acctgattcc tgtctgccgg ga                                    32

<210> SEQ ID NO 142
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 142
aggaggggac ctgaccgcat tcgcaggact tg                                    32

<210> SEQ ID NO 143
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 143
aggaggtagg tgacctgatt cgcgagatcg ta                                    32
```

```
<210> SEQ ID NO 144
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 144
atcgagaaga gtgctgacct gtgttcgcag at                                    32

<210> SEQ ID NO 145
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 145
atacgaagga ttctgggtcg gcgggctctg ct                                    32

<210> SEQ ID NO 146
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 146
atgaccgacc tgcatgcata gaacggacct gt                                    32

<210> SEQ ID NO 147
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 147
ccgggaggcg gacaactgaa ggctactgag ct                                    32

<210> SEQ ID NO 148
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 148
ccggcatcgg tgacctgcac gcatggctca aa                                    32

<210> SEQ ID NO 149
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 149
cccggacacg tatacaagtt cggagagtcg gc                                    32
```

```
<210> SEQ ID NO 150
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 150
cgaatctggc gggatttcaa acgaagtatt ga                                 32

<210> SEQ ID NO 151
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 151
cgacaatgaa gcttaacaac ataagttaat cc                                 32

<210> SEQ ID NO 152
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 152
cgacacaccg ttagtaagca ccggatcggg ta                                 32

<210> SEQ ID NO 153
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 153
cgacacgagg gatagtcagc tgaatagact cg                                 32

<210> SEQ ID NO 154
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 154
cgaatgatga cctgacttgc aacggtcagc ca                                 32

<210> SEQ ID NO 155
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 155
cgaatgatga cctgattcgc aacggccagc ca                                 32

<210> SEQ ID NO 156
```

```
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 156
cgaatgatga cctgattcgc aatggtcagc ca                                 32

<210> SEQ ID NO 157
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 157
cgaattccag atgtgacctg tattcggatt gt                                 32

<210> SEQ ID NO 158
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 158
cgaattccat cgcatttacg acggcttcga cc                                 32

<210> SEQ ID NO 159
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 159
cgaattccat cgcatttact agggcttcga cc                                 32

<210> SEQ ID NO 160
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 160
cgacctgtcg aggggtggca gacgagttgt tc                                 32

<210> SEQ ID NO 161
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 161
cgaccatcag gcttacgtcg aatcgaacga cg                                 32

<210> SEQ ID NO 162
<211> LENGTH: 32
```

```
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 162
cgacccagat ggttgacctg tattcggatt gt                            32

<210> SEQ ID NO 163
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 163
cgactcacat gacctgattg gcgttggccc ca                            32

<210> SEQ ID NO 164
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 164
cgactcatat gacctgattg gcagttggcc ca                            32

<210> SEQ ID NO 165
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 165
cggggacacg aggtggactg atctcgaaat ca                            32

<210> SEQ ID NO 166
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 166
cgggcgaccg acggaagcaa tgaatataag cg                            32

<210> SEQ ID NO 167
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 167
cgggggtcag ggaggcggct aacatagcat gc                            32

<210> SEQ ID NO 168
<211> LENGTH: 32
<212> TYPE: DNA
```

```
<213> ORGANISM: Artificial Sequence
<220> FEATURE:
<223> OTHER INFORMATION: Non-naturally occuring artificial aptamer
      sequence binding to a target molecule.

<400> SEQUENCE: 168
cgggttatga cccattcgct gtaacggcta ac                                    32

<210> SEQ ID NO 169
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 169
cgggtaggga cacgggtgag aaattagtaa ca                                    32

<210> SEQ ID NO 170
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 170
cgggtatggc taggacgtag tcaccggcac ac                                    32

<210> SEQ ID NO 171
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 171
cgggtggtaa caaacggttc acgtgaaacg ct                                    32

<210> SEQ ID NO 172
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 172
cggtaatgga cgcccatcgg ctagtacgga cc                                    32

<210> SEQ ID NO 173
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 173
cggtacatga agggtgtaag acttatcgac cc                                    32

<210> SEQ ID NO 174
<211> LENGTH: 32
<212> TYPE: DNA
<213> ORGANISM: Artificial Sequence
```

```
<220> FEATURE:
<223> OTHER INFORMATION: Non-naturally occuring artificial aptamer
      sequence binding to a target molecule.

<400> SEQUENCE: 174
cggtaacgcg gtgtatatga cctgattcgc tc                                  32

<210> SEQ ID NO 175
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 175
cggtaaggat ataatgacct gattcgctcc ta                                  32

<210> SEQ ID NO 176
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 176
cggtaggcaa tctgcgacag ggtacctggg ta                                  32

<210> SEQ ID NO 177
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 177
cggtagtcga atttgatcga cctgtattcg tc                                  32

<210> SEQ ID NO 178
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 178
cggtagttcc gggaaacgtg actgattcgc ct                                  32

<210> SEQ ID NO 179
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 179
cggtagttcg gaaactgtga cctgattcgc ct                                  32

<210> SEQ ID NO 180
<211> LENGTH: 32
<212> TYPE: DNA
<213> ORGANISM: Artificial Sequence
<220> FEATURE:
```

```
<223> OTHER INFORMATION: Non-naturally occuring artificial aptamer
      sequence binding to a target molecule.

<400> SEQUENCE: 180
cggtgaccaa atcatttgac ctggattcgt ac                                    32

<210> SEQ ID NO 181
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 181
cggtgaggag tcacgctttc ctaccggata gg                                    32

<210> SEQ ID NO 182
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 182
ctcaaagggc cgggaggagg aaccattcgc ga                                    32

<210> SEQ ID NO 183
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 183
ctcgggtagc tggggggtgg cttaagagga tt                                    32

<210> SEQ ID NO 184
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 184
cgttcaagca gtacaggata agcgtccgct ga                                    32

<210> SEQ ID NO 185
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 185
cgttgacctg atcggaggtc gtccaattgg tc                                    32

<210> SEQ ID NO 186
<211> LENGTH: 32
<212> TYPE: DNA
<213> ORGANISM: Artificial Sequence
<220> FEATURE:
<223> OTHER INFORMATION: Non-naturally occuring artificial aptamer
``` sequence binding to a target molecule.

<400> SEQUENCE: 186
cgttgcggcg gagcttggct gatagatcat ga            32

<210> SEQ ID NO 187
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 187
cgttggaaag cggtgacgtt caaggtactg aa            32

<210> SEQ ID NO 188
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 188
cgttgacgag aatggacgag acctgattcg cc            32

<210> SEQ ID NO 189
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 189
cgttgagaga atggacgaga cctgattcgc cg            32

<210> SEQ ID NO 190
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 190
ctaacctgcc gcggatgacc tgtattcgct gt            32

<210> SEQ ID NO 191
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 191
ctaaggaata gtcgacagcg tccgagaggc at            32

<210> SEQ ID NO 192
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 192
ctaatggcgg caaaaaatga cctgcgttcg ca                                    32

<210> SEQ ID NO 193
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 193
ctacctgccg acggatgacc tgtattcgct gt                                    32

<210> SEQ ID NO 194
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 194
ctactcatat gacctgattg gcgttggccc ca                                    32

<210> SEQ ID NO 195
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 195
ctagatgttt agcacggaca agtgaacact gc                                    32

<210> SEQ ID NO 196
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 196
ctaggtggcg aaggtgcggg aacgggatac gt                                    32

<210> SEQ ID NO 197
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 197
gaggaagcaa tgacctgatt ccgttggcct at                                    32

<210> SEQ ID NO 198
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

```
<400> SEQUENCE: 198
gaggacgcaa tgaccggatt ccgttggcct at                                    32

<210> SEQ ID NO 199
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 199
gaggacgatg atgacctggc gattgtcact cg                                    32

<210> SEQ ID NO 200
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 200
gaggacgcaa tgacctgatt ccgttgacct at                                    32

<210> SEQ ID NO 201
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 201
gaggacgtaa tgacctgatt ccgttggcct at                                    32

<210> SEQ ID NO 202
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 202
gaggagtcga tgacctgatt ccgttggcct at                                    32

<210> SEQ ID NO 203
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 203
gcggttgggt ttgacctgat gcgaattgac ct                                    32

<210> SEQ ID NO 204
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 204
```
gcggtcttga cctgacattc acatgtccct gc                                    32

<210> SEQ ID NO 205
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 205
gcgtaacgcg gtgtatatga cctgattcgc tc                                    32

<210> SEQ ID NO 206
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 206
gcgtaaggat acaatgacct gattcgctcc ta                                    32

<210> SEQ ID NO 207
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 207
gcgtaaggtg gcctctgagg acagcaaagg ac                                    32

<210> SEQ ID NO 208
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 208
gcgtagtccg ggaaacgtga cctgattcgc ct                                    32

<210> SEQ ID NO 209
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 209
gcgttaaatg acctgattcg caatcacttg ct                                    32

<210> SEQ ID NO 210
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 210
gctacgcgat acggagaata ccggtaggat ct                                    32

<210> SEQ ID NO 211
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 211
ggtagcgtgg atgacctgaa cattcgccca ca                                    32

<210> SEQ ID NO 212
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 212
tgtagtccgt cgaaacgtga cctgattcgc ct                                    32

<210> SEQ ID NO 213
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 213
tggccagacc gttacaaacg gagtacattc gc                                    32

<210> SEQ ID NO 214
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 214
tgtagttccg gaaacgtgac ctgtattcgc ct                                    32

<210> SEQ ID NO 215
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 215
tgtagttccg gaaactgtga cctgagtcgc ct                                    32

<210> SEQ ID NO 216
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 216
acaatgcgaa ttgacctgac aatgcgaatt ga                                    32

```
<210> SEQ ID NO 217
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 217
ggcgctgtag ccagagttca tctctcgtat cg                                   32

<210> SEQ ID NO 218
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 218
ggcgctgtag ccagagttca tctctcgtat cg                                   32

<210> SEQ ID NO 219
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 219
cgatggtggg aaccgagtac gggtaatccg ac                                   32

<210> SEQ ID NO 220
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 220
cgtaccaggg tgcaagagga gatagatcgc gc                                   32

<210> SEQ ID NO 221
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 221
gagacgtggg aaggagcgga aacttgatct tg                                   32

<210> SEQ ID NO 222
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 222
gcaagtacac gtaggcgctt ggctcgtcac ta                                   32
```

<210> SEQ ID NO 223
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 223
gcacagaaac tgggaagtcc aaacggtcgg tc                                    32

<210> SEQ ID NO 224
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 224
ggagaagcca cggaaaagaa cgcgttggtt gt                                    32

<210> SEQ ID NO 225
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 225
ggagggccat aagcagtgca ccactcgtac tg                                    32

<210> SEQ ID NO 226
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 226
acaatgcgaa ttgacctggg cgaattgacc tg                                    32

<210> SEQ ID NO 227
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 227
acaatgcgaa ttgacctgac cggaacgtgg cg                                    32

<210> SEQ ID NO 228
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 228
acaatgcgaa ttgacctgga caatgcgaat tg                                    32

```
<210> SEQ ID NO 229
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 229
acaatgcgaa ttgacctggc gatgcgaatt ga                                32

<210> SEQ ID NO 230
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 230
acaatgcgaa ttgacctggc gaattgacct gg                                32

<210> SEQ ID NO 231
<211> LENGTH: 19
<212> TYPE: DNA
<213> ORGANISM: Artificial Sequence
<220> FEATURE:
<223> OTHER INFORMATION: Artificial, non-naturally occuring 5' primer
      sequence

<400> SEQUENCE: 231
taatacgact cactatagg                                               19

<210> SEQ ID NO 232
<211> LENGTH: 19
<212> TYPE: DNA
<213> ORGANISM: Artificial Sequence
<220> FEATURE:
<223> OTHER INFORMATION: Artificial, non-naturally occuring 3' primer
      sequence

<400> SEQUENCE: 232
gacaatgcga attgacctg                                               19

<210> SEQ ID NO 233
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 233
gacgtagggt gtgggtacgg tttggggtcg ga                                32

<210> SEQ ID NO 234
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 234
gtgtagggtg tgggtacggc gtaggggggg aa                                32

<210> SEQ ID NO 235
```

```
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 235
gacgtagggt gagggtacgg ttgggggtcg ga                                   32

<210> SEQ ID NO 236
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 236
gacgtagggt gtgggtacgg ctgggggtcg ga                                   32

<210> SEQ ID NO 237
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 237
gacgtagggt gtgggtacgg ttgtgggtcg ga                                   32

<210> SEQ ID NO 238
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 238
tcgtagggtg tgggtacggt gttgggggtcg tt                                  32

<210> SEQ ID NO 239
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 239
gacgcagggt gtgggtacgg ttgggggtcg ga                                   32

<210> SEQ ID NO 240
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 240
gacgtagggt gtgggtacgg ttagggtcg ga                                    32

<210> SEQ ID NO 241
<211> LENGTH: 32
```

```
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 241
gacgtagggc gtgggtacgg ttgggggtcg ga                                   32

<210> SEQ ID NO 242
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 242
gacgtagggt gtgggtacgg ttgggggtcg ga                                   32

<210> SEQ ID NO 243
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 243
tgtctatcta gatgcttcct gcacaccect tc                                   32

<210> SEQ ID NO 244
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 244
tgtgcctgta agtgcgaatc actcgtctct ct                                   32

<210> SEQ ID NO 245
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 245
ttaacgcacc cacacgacac tacgaaccac ga                                   32

<210> SEQ ID NO 246
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 246
tgtgtctacg ctcccccgtc accacctatc tt                                   32

<210> SEQ ID NO 247
<211> LENGTH: 32
<212> TYPE: DNA
```

-continued

<213> ORGANISM: Artificial Sequence
<220> FEATURE:
<223> OTHER INFORMATION: Non-naturally occuring artificial aptamer
      sequence binding to a target molecule.

<400> SEQUENCE: 247
ttacatcccg cttacgagtg taggattata cg                                    32

<210> SEQ ID NO 248
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 248
ttaccctgtt cagagagaca aaacgtttcc tg                                    32

<210> SEQ ID NO 249
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 249 tagccccct atacaacgtc ctcagttacg ag                                     32

<210> SEQ ID NO 250
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 250
gtacgaggcg atagaccaaa cagctgccca aa                                    32

<210> SEQ ID NO 251
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 251
ttcataccac caaagcgtat ttctgacgcc ag                                    32

<210> SEQ ID NO 252
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 252
ttccacggat gcacccatat cacgccacaa cg                                    32

<210> SEQ ID NO 253
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 253
ttaggctgct cttcgcttcc atcaaactac cc                                    32

<210> SEQ ID NO 254
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 254
ttcaatgaac ccctataggc actcggtata cg                                    32

<210> SEQ ID NO 255
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 255
ttcctgtctc ctccacgtgt tccgttatta cg                                    32

<210> SEQ ID NO 256
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 256
ttcgacatgc ggaggaacga acccacacac ct                                    32

<210> SEQ ID NO 257
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 257
ttcgcgatgt ttagccctaa acccaccccc gt                                    32

<210> SEQ ID NO 258
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 258
ttcgcgtact aggacaccgc ctcctcaccc ac                                    32

<210> SEQ ID NO 259
<211> LENGTH: 32
<212> TYPE: DNA
<213> ORGANISM: Artificial Sequence
<220> FEATURE:

```
<223> OTHER INFORMATION: Non-naturally occuring artificial aptamer
      sequence binding to a target molecule.

<400> SEQUENCE: 259
ttcggcctgt ggaactatgc tgatattatc cc                                    32

<210> SEQ ID NO 260
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 260
gacgagggtg tgggtacggt tgggggtcgg ta                                    32

<210> SEQ ID NO 261
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 261
tcgtcccaat tatgggcaca ttggcatcat ag                                    32

<210> SEQ ID NO 262
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 262
ttgcattaaa cgccaagcgg aaaccctgtg cg                                    32

<210> SEQ ID NO 263
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 263
ttctcgtctc actccaccct cacgtagagt gc                                    32

<210> SEQ ID NO 264
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 264
ttgatagcaa aacgaagaaa cctcgccccc gc                                    32

<210> SEQ ID NO 265
<211> LENGTH: 32
<212> TYPE: DNA
<213> ORGANISM: Artificial Sequence
<220> FEATURE:
<223> OTHER INFORMATION: Non-naturally occuring artificial aptamer
``` sequence binding to a target molecule.

<400> SEQUENCE: 265
ttgatcaccg caatatcatc cgccccaacc ca                                        32

<210> SEQ ID NO 266
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 266
ttgcctaatc aggcctaagt tcgttcttat cg                                        32

<210> SEQ ID NO 267
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 267
ttgcgcccaa tattggccca acccaccacc ag                                        32

<210> SEQ ID NO 268
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 268
ttggcttccc atcgcgcctc attccgcttt at                                        32

<210> SEQ ID NO 269
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 269
ttgtaaacac caacccaaac gacggagcat cg                                        32

<210> SEQ ID NO 270
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 270
ttttgcataa gaatcgaggt gcttaaatag cg                                        32

<210> SEQ ID NO 271
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 271
tttgcacgcc cacacccgtc ttgtcgcagc tc                                    32

<210> SEQ ID NO 272
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 272
aatgatcaca aaggcgactg agtcagaaca aa                                    32

<210> SEQ ID NO 273
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 273
caagcgacac ccacccagcc cattccaacc ct                                    32

<210> SEQ ID NO 274
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 274
caccaccctg cctatcgcca cttgttctgc ct                                    32

<210> SEQ ID NO 275
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 275
atgttcactt gacggatgat acaccctcta ag                                    32

<210> SEQ ID NO 276
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 276
cctatgttct aacaccagta aaggttgtgg ct                                    32

<210> SEQ ID NO 277
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

```
<400> SEQUENCE: 277
ccgcgaccct gccctccctc tcgttctctg ct                                    32

<210> SEQ ID NO 278
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 278
cgtatagcaa tacccgtcgc ctattcccca gt                                    32

<210> SEQ ID NO 279
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 279
ctacaaaatg taaccatgcg agtgtccttt cc                                    32

<210> SEQ ID NO 280
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 280
cttaccatcc actccccact ctctgtatac gc                                    32

<210> SEQ ID NO 281
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 281
tcaactgcca tgtctgccac ccacctcttt at                                    32

<210> SEQ ID NO 282
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 282
ggtgcttgga ctcgcacgac aaatacgcta aa                                    32

<210> SEQ ID NO 283
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 283
```
tgttcacccc ccaattgtcc cactggatat cg                              32

<210> SEQ ID NO 284
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 284
ttaagtccta gcctggtccc acacttgaac ct                              32

<210> SEQ ID NO 285
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 285
ttttgctaga gataaccgtg ctagagatca ca                              32

<210> SEQ ID NO 286
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 286
gtacgaggcg atagaccaaa cagctgccca aa                              32

<210> SEQ ID NO 287
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 287
tcgcgctgca tctatagcac ttcctgattt tg                              32

<210> SEQ ID NO 288
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 288
tcgctcagag tcgcgcgatc cataatgaac ag                              32

<210> SEQ ID NO 289
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 289
tcgatactct acactcgtga gcgtgtacac ag                32

<210> SEQ ID NO 290
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 290
tcgatcccct gactccttgt ataaagtccc ag                32

<210> SEQ ID NO 291
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 291
tcgcacgctg acccacccac tctttagcga ct                32

<210> SEQ ID NO 292
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 292
tcgccaaatt gcgataaaac ccttcgtgct ag                32

<210> SEQ ID NO 293
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 293
tcgccccaaa cactaactcc ttggaacctc ac                32

<210> SEQ ID NO 294
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 294
tcgtcagaaa cgcgcgctat tacacttagc tg                32

<210> SEQ ID NO 295
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 295
tcttggtcgc ttcggacgcc cgattcaatt ag                32

<210> SEQ ID NO 296
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 296
tctgcgctac accctcaacc atccgctgaa gg                                   32

<210> SEQ ID NO 297
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 297
tgaggcgcaa cgttattcgc acccacacag tc                                   32

<210> SEQ ID NO 298
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 298
tgaacccaag cttcacttgt tatggtgcct ag                                   32

<210> SEQ ID NO 299
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 299
tgacccgcta ctatcttgcg catcatataa cg                                   32

<210> SEQ ID NO 300
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 300
tgcctacgta aagcacatca atgcttgtgt ag                                   32

<210> SEQ ID NO 301
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 301
tgcctcttca cggatacttg cgaatgatag ga                                   32

<210> SEQ ID NO 302
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 302
tgccttagtt gtgctaacaa ctcatccaca cc                                     32

<210> SEQ ID NO 303
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 303
tgcgaaggag gactgcccaa actacgacac ta                                     32

<210> SEQ ID NO 304
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 304
tgcaagcagc actaacgaca acaggtgcca cg                                     32

<210> SEQ ID NO 305
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 305
tgcacaatca ctgtgcgctc atcaactagc ag                                     32

<210> SEQ ID NO 306
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 306
tgccaaagca caggaacgat cccaaatcaa cg                                     32

<210> SEQ ID NO 307
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 307
tgcccacagc acgtttctct ccctgcaata ag                                     32

```
<210> SEQ ID NO 308
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 308
tgctgaatat ccccccagc ctcccccaca cc                                      32

<210> SEQ ID NO 309
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 309
tgctgtttct accgctgatc acccctttgg cc                                      32

<210> SEQ ID NO 310
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 310
tgcgcacagc atactattgt ctcgatacca gt                                      32

<210> SEQ ID NO 311
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 311
tgcgctgtac taactcagaa aacacagtca cg                                      32

<210> SEQ ID NO 312
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 312
tgcggagcaa ttttacaagc tccctgtcca ag                                      32

<210> SEQ ID NO 313
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 313
tgctaagcga taagctaacc taccccacc tt                                       32

<210> SEQ ID NO 314
```

```
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 314
tgctacgccg aactacccgt taaggtaccc at                                    32

<210> SEQ ID NO 315
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 315
tggaccaacc agtaccacct tgactattaa tc                                    32

<210> SEQ ID NO 316
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 316
tggacgctcc ccgtcgaacg caatatctta ca                                    32

<210> SEQ ID NO 317
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 317
tggcacgcct ctcaacgtcc accaccactt tt                                    32

<210> SEQ ID NO 318
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 318
tggcgcctga ataggcccta acttattcac ag                                    32

<210> SEQ ID NO 319
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 319
tggctcaccg caaatgcaac cgctcccacc ca                                    32

<210> SEQ ID NO 320
<211> LENGTH: 32
```

```
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 320
tgtaccccac agctgtgcat cgcactcccg cg                            32

<210> SEQ ID NO 321
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 321
tggttatcaa cgtgtagatg atgctcactc ac                            32

<210> SEQ ID NO 322
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 322
tacgctatag tccgcgtcca cgttcacgca ag                            32

<210> SEQ ID NO 323
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 323
tcgaaagctc gctacttcgc tgcccgttcc cg                            32

<210> SEQ ID NO 324
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 324
tccgtgttta gccactccct gagcgcattt cg                            32

<210> SEQ ID NO 325
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 325
tcctccatcc gatggaaccc gcaactttca tg                            32

<210> SEQ ID NO 326
<211> LENGTH: 32
<212> TYPE: DNA
```

```
<213> ORGANISM: Artificial Sequence
<220> FEATURE:
<223> OTHER INFORMATION: Non-naturally occuring artificial aptamer
      sequence binding to a target molecule.

<400> SEQUENCE: 326
tcgcgctgca tctatagcac ttcctgattt tg                                    32

<210> SEQ ID NO 327
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 327
tcgctcagag tcgcgcgatc cataatgaac ag                                    32

<210> SEQ ID NO 328
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 328
tcgatactct acactcgtga gcgtgtacac ag                                    32

<210> SEQ ID NO 329
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 329
tcgatcccct gactccttgt ataaagtccc ag                                    32

<210> SEQ ID NO 330
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 330
tcgcacgctg acccacccac tctttagcga ct                                    32

<210> SEQ ID NO 331
<211> LENGTH: 32
<212> TYPE: DNA
<213> ORGANISM: Artificial Sequence
<220> FEATURE:
<223> OTHER INFORMATION: Non-naturally occuring artificial aptamer
      sequence binding to a target molecule.

<400> SEQUENCE: 331
tcgccaaatt gcgataaaac ccttcgtgct ag                                    32

<210> SEQ ID NO 332
<211> LENGTH: 32
<212> TYPE: DNA
<213> ORGANISM: Artificial Sequence
```

-continued

```
<220> FEATURE:
<223> OTHER INFORMATION: Non-naturally occuring artificial aptamer
      sequence binding to a target molecule.

<400> SEQUENCE: 332
tcgccccaaa cactaactcc ttggaacctc ac                                      32
```